(12) United States Patent
Kando et al.

(10) Patent No.: US 6,630,592 B1
(45) Date of Patent: Oct. 7, 2003

(54) PROCESSES FOR PRODUCTION OF OXADIAZOLINE DERIVATIVES

(75) Inventors: Yasuyuki Kando, Tsukuba (JP); Toshiyuki Kiji, Tsukuba (JP)

(73) Assignee: Sumitomo Chemical Takeda Agro Company, Limited, Tokyo (JP)

( * ) Notice: Subject to any disclaimer, the term of this patent is extended or adjusted under 35 U.S.C. 154(b) by 0 days.

(21) Appl. No.: 10/148,493

(22) PCT Filed: Nov. 17, 2000

(86) PCT No.: PCT/JP00/08108

§ 371 (c)(1),
(2), (4) Date: May 29, 2002

(87) PCT Pub. No.: WO01/40203

PCT Pub. Date: Jun. 7, 2001

(30) Foreign Application Priority Data

Nov. 30, 1999 (JP) .............................. 11/340606
Aug. 1, 2000 (JP) ........................................ 2000/233264

(51) Int. Cl.[7] .................... C07D 413/04; C07D 271/06; A61K 31/4245
(52) U.S. Cl. .................... 546/269.1; 514/340; 514/364; 546/269.1; 548/131
(58) Field of Search ................................ 514/341, 364, 514/386; 546/269.4; 548/131, 312.4

(56) References Cited

U.S. PATENT DOCUMENTS 6,107,314 A * 8/2000 Wu .............................. 514/341

FOREIGN PATENT DOCUMENTS

| JP | 4-275277 | 9/1992 |
| JP | 11-171702 | 6/1999 |
| WO | 95/11014 | 4/1995 |
| WO | 98/57969 | 12/1998 |

OTHER PUBLICATIONS

Frank Bell, "5-Amino-1-aryl-3-methylpyrazoles", J. Chem. pp. 285-287, (1941).

* cited by examiner

Primary Examiner—Alan L. Rotman
Assistant Examiner—Janet L. Coppins
(74) Attorney, Agent, or Firm—Wenderoth, Lind & Ponack, L.L.P.

(57) ABSTRACT

A process as represented by reaction scheme:

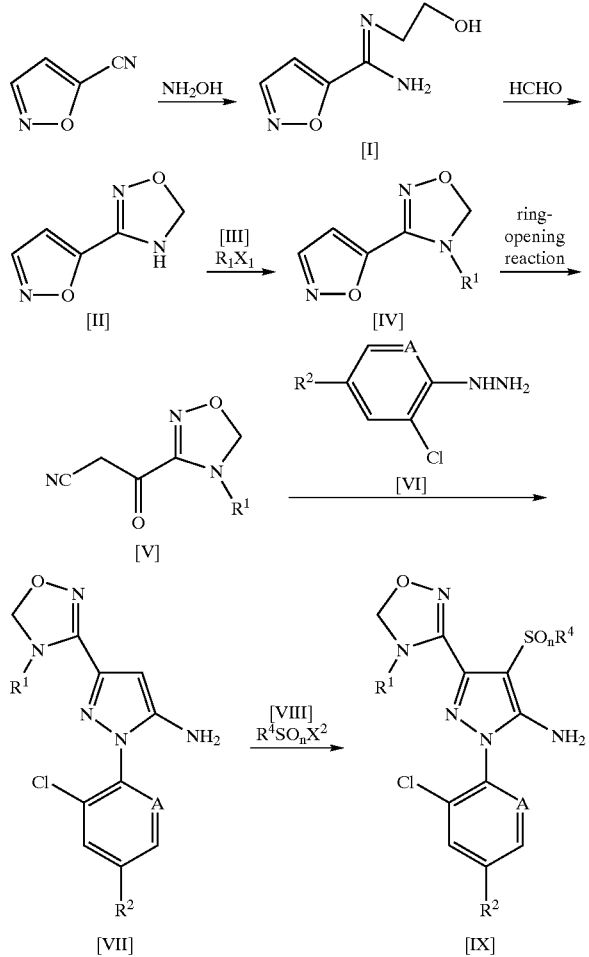

which permits industrial mass production of $\Delta^2$-1,2,4-oxadiazoline derivatives having excellent insecticidal effects or salts thereof in high yield with advantage, [wherein $X^1$ is halogeno; $R^1$ is optionally substituted alkyl, optionally substituted acyl, or ClCO; $R^2$ is (1) halogeno, (2) $C_{1-6}$ haloalkyl, (3) $C_{1-6}$ haloalkoxy, or (4) phenyl optionally substituted with $C_{1-6}$ haloalkyl; A is nitrogen or =CR$^3$— (wherein $R^3$ is Cl or CN); $R^4$ is $C_{1-6}$ alkyl or $C_{1-6}$ haloalkyl; n is 0, 1 or 2; and $X^2$ is halogeno].

18 Claims, No Drawings

PROCESSES FOR PRODUCTION OF OXADIAZOLINE DERIVATIVES

This application is a 371 of PCT/JP00/08108 filed Nov. 17, 2000.

FIELD OF THE INVENTION

The present invention relates to a process for producing oxadiazoline derivatives (for example, compounds [IX], [IX$_a$] and the like described hereinafter), intermediates for synthesis of the oxadiazoline derivatives, and a process for producing the intermediates. The oxadiazoline derivatives are useful as insecticides and acaricides.

BACKGROUND ART

So far, known processes for producing $\Delta^2$-1,2,4-oxadiazoline derivatives having a pyrazol substituent at the 3-position thereof include e.g. a process for producing the derivatives from cyanopyrazol derivatives (JP-A 10-152476).

However, a process for synthesizing 3-pyrazolyl-$\Delta^2$-1,2,4-oxadiazoline derivatives having various kinds of substituents on the nitrogen atom at the 4-position of the oxadiazoline ring is still not known, and at present, there is no satisfactory process as a general or industrial process for synthesis of $\Delta^2$-1,2,4-oxadiazoline derivatives useful as insecticides and acaricides.

OBJECT OF THE INVENTION

An object of the present invention is to provide a satisfactory process as a general or industrial process for synthesizing $\Delta^2$-1,2,4-oxadiazoline derivatives useful as insecticides and acaricides.

SUMMARY OF THE INVENTION

The present inventors extensively studied for solving the problem described above, and unexpectedly found that 3-pyrazolyl-$\Delta^2$-1,2,4-oxadiazoline derivatives can be synthesized in high yield by the ring transformation reaction of 3-isoxazolyl-$\Delta^2$-1,2,4-oxadiazoline derivatives, and the present invention was thereby completed.

That is, the present invention relates to:

1. A process for producing isoxazole-5-carboxamide oxime represented by formula [I]:

[I]

or a salt thereof, which comprises reacting 5-cyanoisoxazole with hydroxylamine or a salt thereof;

2. A process for producing 3-(5-isoxazolyl)-$\Delta^2$-1,2,4-oxadiazoline represented by formula [II]:

[II]

or a salt thereof, which comprises reacting isoxazole-5-carboxamide oxime represented by formula [I]:

[I]

or a salt thereof with formaldehyde or an equivalent thereof;

3. A process for producing a compound represented by formula [IV]:

[IV]

wherein R$^1$ represents an optionally substituted alkyl group, an optionally substituted acyl group or chlorocarbonyl group (ClCO), or a salt thereof, which comprises reacting 3-(5-isoxazolyl)-$\Delta^2$-1,2,4-oxadiazoline represented by formula [II]:

[II]

or a salt thereof with a compound represented by formula [III]:

R$^1$X$^1$  [III]

wherein X$^1$ represents a halogen atom, and R$^1$ is as defined above, or an equivalent thereof or a salt thereof;

4. A process for producing a compound represented by formula [V]:

[V]

wherein R$^1$ is as defined in the above 3, or a salt thereof, which comprises subjecting a compound represented by formula [IV]:

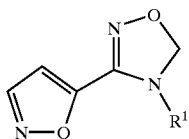
[IV]

wherein R¹ is as defined in the above item 3, or a salt thereof to the ring-opening reaction of the isoxazole ring;

5. A process for producing a compound represented by formula [VII]:

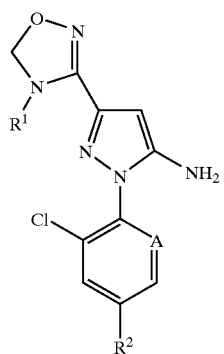
[VII]

wherein R¹ is as defined in the above item 3, and R² represents (1) halogen, (2) $C_{1-6}$ haloalkyl group, (3) $C_{1-6}$ haloalkoxy group or (4) phenyl group optionally substituted with a $C_{1-6}$ haloalkyl group] or a salt thereof, which comprises reacting a compound represented by formula [V]:

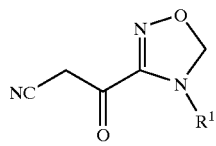
[V]

wherein R¹ is as defined in the above item 3, or a salt thereof with a compound represented by formula [VI]:

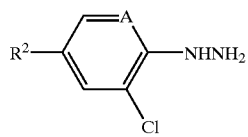
[VI]

wherein A represents a nitrogen atom or

(wherein R³ represents chlorine atom or cyano group, and the other symbol is as defined above, or a salt thereof;

6. A process for producing a compound represented by formula [IX]:

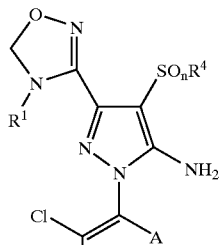
[IX]

wherein R¹ is as defined in the above item 3, R² and A are as defined in the above item 5, and R⁴ represents a $C_{1-6}$ alkyl group or $C_{1-6}$ haloalkyl group, or a salt thereof, which comprises reacting a compound represented by formula [VII]:

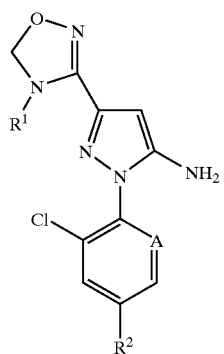
[VII]

wherein R¹ is as defined in the above item 3, and R² and A are as defined in the above item 5, or a salt thereof with a compound represented by the formula [VIII]:

$R^4SO_nX^2$ [VIII]

wherein R⁴ is as defined above, n is 0, 1 or 2, and X² represents a halogen atom;

7. A process for producing a compound represented by formula [IV$_b$]:

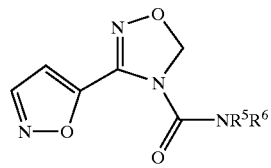
[IVb]

wherein R⁵ and R⁶ each represent a $C_{1-6}$ alkyl group, or R⁵ and R⁶, together with their adjacent nitrogen atom, represent a cyclic amino group, or a salt thereof, which comprises reacting a compound represented by formula [IV$_a$]:

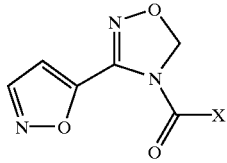

[IVa]

wherein X represents a chlorine atom, 1-chloroethoxy group, chloromethoxy group or phenoxy group, or a salt thereof with an amine represented by formula [X]:

R⁵R⁶NH  [X]

wherein the symbols are as defined above, or a salt thereof;

8. A process for producing a compound represented by formula [V$_a$]:

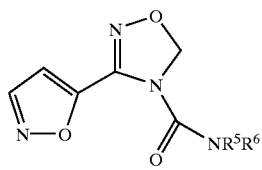

[Va]

wherein $R^5$ and $R^6$ are as defined in the above item 7, or a salt thereof, which comprises subjecting a compound represented by formula [IV$_b$]:

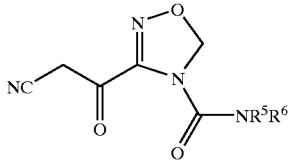

[IVb]

wherein $R^5$ and $R^6$ are as defined in the above item 7, or a salt thereof to the ring-opening reaction of the isoxazole ring;

9. A process for producing a compound represented by formula [VII$_a$]:

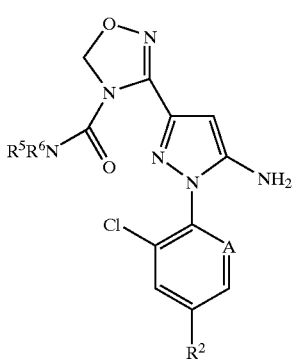

[VIIa]

wherein $R^2$ and A are as defined in the above item 5, and $R^5$ and $R^6$ are as defined in the above item 7, or a salt thereof, which comprises reacting a compound represented by formula [V$_a$]:

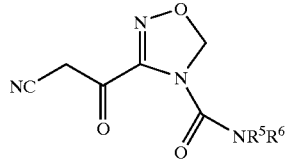

[Va]

wherein $R^5$ and $R^6$ are as defined in the above item 7, or a salt thereof with a compound represented by formula [VI]:

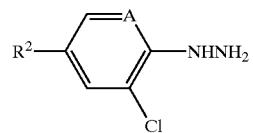

[VI]

wherein $R^2$ and A are as defined in the above item 5, or a salt thereof;

10. A process for producing a compound represented by formula [IX$_a$]:

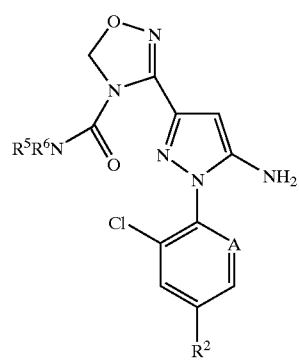

[IXa]

wherein $R^2$ and A are as defined in the above item 5, $R^4$ and n are as defined in the above item 6, and $R^5$ and $R^6$ are as defined in the above item 7, or a salt thereof, which comprises reacting a compound represented by formula [VII$_a$]:

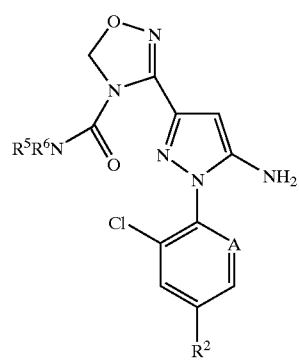

[VIIa]

wherein $R^2$ and A are as defined in the above item 5, and $R^5$ and $R^6$ are as defined in the above item 7, or a salt thereof with a compound represented by formula [VIII]:

R⁴SO$_n$X²  [VIII]

wherein $R^4$, n and $X^2$ are as defined in the above item 6;

11. 3-(5-Isoxazolyl)-$\Delta^2$-1,2,4-oxadiazoline represented by formula [II]:

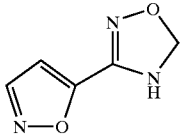

[II]

or a salt thereof;

12. A compound represented by formula [IV]:

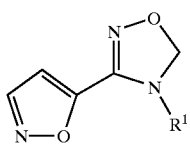

[IV]

wherein $R^1$ is as defined in the above item 3, or a salt thereof;

13. A compound represented by formula [V]:

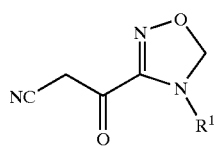

[V]

wherein $R^1$ is as defined in the above item 3, or a salt thereof;

14. A compound represented by formula [VII]:

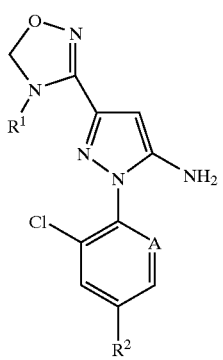

[VII]

wherein $R^1$ is as defined in the above item 3, and $R^2$ and A are as defined in the above item 5, or a salt thereof;

15. A compound represented by formula [$IV_a$]:

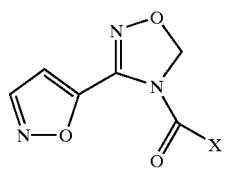

[IVa]

wherein X is as defined in the above item 7, or a salt thereof;

16. A compound represented by formula [$IV_b$]:

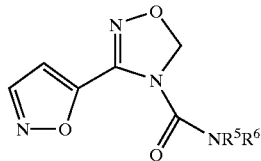

[IVb]

wherein $R^5$ and $R^6$ are as defined in the above item 7, or a salt thereof;

17. A compound represented by formula [$V_a$]:

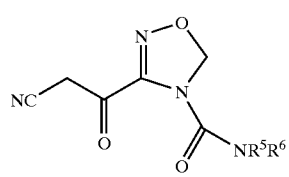

[Va]

wherein $R^5$ and $R^6$ are as defined in the above item 7, or a salt thereof; and 18. A compound represented by formula [$VII_a$]:

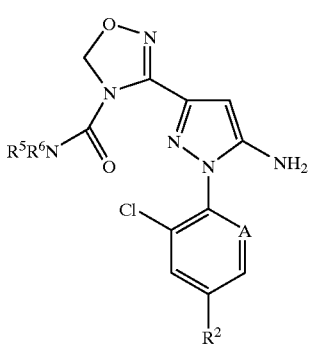

[VIIa]

wherein $R^2$ and A are as defined in the above item 5, and $R^5$ and $R^6$ are as defined in the above item 7, or a salt thereof.

DETAILED DESCRIPTION OF THE INVENTION

In the formulae above, the alkyl group in the optionally substituted alkyl group represented by $R^1$ includes e.g. $C_{1-6}$ alkyl groups such as methyl, ethyl, n-propyl, isopropyl, n-butyl, isobutyl, sec-butyl and tert-butyl.

The substituent on the alkyl group include hydroxyl group, amino group, mono- or di-$C_{1-6}$ alkylamino group (e.g., methylamino, ethylamino, propylamino, dimethylamino, diethylamino and the like), $C_{1-6}$ alkoxy group (e.g., methoxy, ethoxy, propoxy, isopropoxy, butoxy and the like), $C_{1-6}$ alkylthio group (e.g., methylthio, ethylthio, n-propylthio, isopropylthio, butylthio and the like), halogen atom (e.g., fluorine, chlorine, bromine, iodine), carboxyl group, nitro group, cyano group and the like. The substituent is particularly preferably a $C_{1-6}$ alkoxy group.

The number of substituent is 1 to 6, preferably 1 to 3, within the replaceable range.

The acyl group in the optionally substituted acyl group represented by $R^1$ includes $C_{1-20}$ acyl groups derived from carboxylic acids, and examples thereof include (1) formyl, (2) alkanoyl group, preferably $C_{2-10}$ alkanoyl group (e.g., $C_{1-9}$ alkyl-carbonyl group such as acetyl, propionyl, butyryl, isobutyryl, pentanoyl, hexanoyl, heptanoyl, pivaloyl and the like), (3) cycloalkanoyl group, preferably $C_{4-10}$ cycloalkanoyl group (e.g., cyclopropyl carbonyl, cyclobutyl carbonyl, cyclopentyl carbonyl, cyclohexyl carbonyl and the like), (4) alkenyl carbonyl group, preferably $C_{3-10}$ alkenyl carbonyl group (e.g., acryloyl, allyl carbonyl, isopropenyl carbonyl, isobutenyl carbonyl, 1-methyl allyl carbonyl, cinnamoyl and the like), (5) alkynyl carbonyl group, preferably $C_{3-7}$ alkynyl carbonyl group (e.g., propargyl carbonyl, 2-butynyl carbonyl, 3-butynyl carbonyl, 3-pentynyl carbonyl and the like), (6) aryl carbonyl group, preferably $C_{7-14}$ aryl-carbonyl group (e.g., benzoyl, 1-naphthoyl, 2-naphthoyl and the like), (7) alkoxy carbonyl group, preferably $C_{2-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like), (8) aryloxy carbonyl group, preferably $C_{7-14}$ aryloxy-carbonyl group (e.g., phenoxy carbonyl group), (9) aralkyl carbonyl group, preferably $C_{8-19}$ aralkyl-carbonyl group (e.g., phenyl-$C_{1-4}$ alkyl carbonyl such as benzyl carbonyl, phenetyl carbonyl and phenyl propyl carbonyl, and naphthyl-$C_{1-4}$ alkyl carbonyl such as benzhydryl carbonyl and 1-naphthyl ethyl carbonyl), (10) aralkyloxy carbonyl group, preferably $C_{8-19}$ aralkyloxy carbonyl group (e.g., phenyl-$C_{1-4}$ alkyloxy carbonyl such as benzyloxy carbonyl, phenetyloxy carbonyl and phenyl propyloxy carbonyl), (11) carbamoyl group, and (12) cyclic aminocarbonyl group (e.g., 1-pyrrolidinocarbonyl, piperidinocarbonyl, morpholinocarbonyl, thiomorpholinocarbonyl and 1-perhydroazepinyl carbonyl and the like).

When the acyl group is an alkanoyl group, alkenyl carbonyl group or alkynyl carbonyl group, the group may have 1 to 6 (preferably 1 to 3) substituents such as hydroxyl group, amino group, mono- or di-$C_{1-6}$ alkylamino group (e.g., methylamino, ethylamino, propylamino, dimethylamino, diethylamino and the like), $C_{1-6}$ alkoxy group (e.g., methoxy, ethoxy, propoxy, isopropoxy, butoxy and the like), $C_{1-6}$ alkylthio group (e.g., methylthio, ethylthio, n-propylthio, isopropylthio, n-butylthio and the like), halogen atom (e.g., fluorine, chlorine, bromine, iodine), carboxyl group, nitro group, cyano group, phenyl group and the like.

When the acyl group is cycloalkanoyl group, aryl carbonyl group, alkoxycarbonyl group, aryloxy carbonyl group, aralkyl carbonyl group or aralkyloxy carbonyl group, the group may have 1 to 5 (preferably 1 to 3) substituents such as hydroxyl group, amino group, mono- or di-$C_{1-6}$ alkylamino group (e.g., methylamino, ethylamino, propylamino, dimethylamino, diethylamino and the like), $C_{1-6}$ alkoxy group (e.g., methoxy, ethoxy, propoxy, isopropoxy, butoxy and the like), $C_{1-6}$ alkylthio group (e.g., methylthio, ethylthio, n-propylthio, isopropylthio, n-butylthio and the like), halogen atom (e.g., fluorine, chlorine, bromine, iodine), carboxyl group, nitro group, cyano group, phenyl group, $C_{1-6}$ alkyl group (e.g., methyl, ethyl, n-propyl, isopropyl, n-butyl, isobutyl, sec-butyl, tert-butyl and the like), $C_{2-6}$ alkenyl group (e.g., vinyl, allyl, 1-propenyl, 1-butenyl, 2-butenyl and the like), $C_{2-6}$ alkynyl group (e.g., ethynyl, 1-propynyl, propargyl, 1-butynyl and the like) and the like When the acyl group is a carbamoyl group, the group may have 1 or 2 substituents such as (1) $C_{1-6}$ alkyl group (e.g., methyl, ethyl, n-propyl, isopropyl, n-butyl, isobutyl, sec-butyl, tert-butyl and the like), (2) $C_{3-9}$ cycloalkyl group (e.g., cyclopropyl, cyclobutyl, cyclopentyl, cyclohexyl and the like), (3) $C_{2-6}$ alkenyl group (e.g., vinyl, allyl, 1-propenyl, 1-butenyl, 2-butenyl and the like), (4) $C_{2-6}$ alkynyl group (e.g., ethynyl, 1-propynyl, propargyl, 1-butynyl and the like), (5) hydroxyl group, (6) $C_{1-6}$ alkoxy group (e.g., methoxy, ethoxy, propoxy, isopropoxy, butoxy and the like), (7) amino group, (8) mono- or di-$C_{1-6}$ alkyl amino group (e.g., methylamino, ethylamino, propylamino, dimethylamino, diethylamino and the like), (9) cyclic amino group (e.g., 1-pyrrolidino, piperidino, morpholino, 4-methyl-1-piperazino and the like) or (10) phenyl group, and the substituent, together with the nitrogen atom to which it is bonded, may form a cyclic amino group (e.g., 1-pyrrolidino, piperidino, morpholino, thiomorpholino, 4-methyl-1-piperazino and the like). Further, the substituent may be substituted with 1 to 6 (preferably 1 to 3) substituents selected from hydroxyl group, amino group, mono- or di-$C_{1-6}$ alkylamino group (e.g., methylamino, ethylamino, propylamino, dimethylamino, diethylamino and the like), $C_{1-6}$ alkoxy group (e.g., methoxy, ethoxy, propoxy, isopropoxy, butoxy and the like), $C_{1-6}$ alkylthio group (e.g., methylthio, ethylthio, n-propylthio, isopropylthio, n-butylthio and the like), halogen atom (e.g., fluorine, chlorine, bromine, iodine), phenyl group, carboxyl group, nitro group and cyano group.

$R^1$ is, out of those groups described above, preferably an optionally substituted alkyl group, an optionally substituted alkanoyl group, an optionally substituted cycloalkanoyl group, an optionally substituted alkenyl carbonyl group, an optionally substituted aryl carbonyl group, an optionally substituted alkoxy carbonyl group or an optionally substituted carbamoyl group, more preferably an optionally substituted carbamoyl group. $R^1$ is particularly preferably (1) a $C_{1-6}$ alkyl group optionally substituted with one to three $C_{1-6}$ alkoxy, (2) a $C_{2-10}$ alkanoyl group optionally substituted with one to three amino being optionally substituted with one or two $C_{1-6}$ alkyl groups, $C_{1-6}$ alkoxy, phenyl or halogen, (3) a $C_{4-10}$ cycloalkanoyl group, (4) a $C_{3-10}$ alkenyl carbonyl group, (5) benzoyl group, (6) carbamoyl group optionally substituted with one or two $C_{1-6}$ alkyl, $C_{3-9}$ cycloalkyl, $C_{2-6}$ alkenyl, $C_{2-6}$ alkynyl, phenyl, amino optionally substituted with one or two $C_{1-6}$ alkyl, cyclic amino (for example, pyrrolidino, piperidino), hydroxyl or $C_{1-6}$ alkoxy, which may be substituted with one to three substituents selected from amino optionally substituted with one or two $C_{1-6}$ alkyl, phenyl, halogen and $C_{1-6}$ alkyl, (7) a cyclic amino-carbonyl group (for example, pyrrolidinocarbonyl, piperidinocarbonyl, 1-perhydroazepinyl carbonyl, 4-methyl-1-piperazinyl carbonyl, morpholinocarbonyl), (8) a $C_{2-6}$ alkoxy-carbonyl group optionally substituted with one to three halogen atoms, (9) a $C_{7-14}$ aryloxy carbonyl group or (10) a formyl group. More preferable groups represented by $R^1$ include a di-$C_{1-6}$ alkyl carbamoyl group, morpholinocarbonyl group, 1-chloroethoxy carbonyl group, chloromethoxy carbonyl group, phenoxy carbonyl group and the like.

The halogen atom in $X^1$ and $R^2$ includes fluorine, chlorine, bromine and iodine. Particularly, chlorine is preferable.

The $C_{1-6}$ haloalkyl group represented by $R^2$ includes e.g. a $C_{1-6}$ alkyl group substituted with one to ten (preferably one to five) halogens (for example, fluorine, chlorine, bromine, iodine), such as chloromethyl, fluoromethyl, bromomethyl, 2-chloroethyl, dichloromethyl, trichloromethyl, trifluoromethyl, 2,2,2-trifluoroethyl, pentafluoroethyl, heptafluoropropyl, nonafluorobutyl and the like. Particularly, trifluoromethyl is preferable.

The $C_{1-6}$ haloalkoxy group represented by $R^2$ includes e.g. a $C_{1-6}$ alkoxy group substituted with one to ten (preferably one to five) halogens (for example, fluorine, chlorine, bromine, iodine), such as chloromethoxy, fluoromethoxy, bromomethoxy, 2-chloroethoxy, dichloroethoxy, trichloromethoxy, trifluoromethoxy, 2,2,2-trifluoroethoxy, pentafluoroethoxy, heptafluoropropoxy and nonafluorobutoxy. Particularly, trifluoromethoxy is preferable.

The $C_{1-6}$ haloalkyl group in the "phenyl group optionally substituted with a $C_{1-6}$ haloalkyl group" represented by $R^2$ includes the $C_{1-6}$ haloalkyl groups described above. The number of substituents on the phenyl group is 1 to 5, preferably 1 to 3. In particular, a phenyl group optionally substituted with one to three trifluoromethyl groups is preferable.

In particular, A is preferably

The $C_{1-6}$ alkyl group represented by $R^4$ includes the $C_{1-6}$ alkyl groups exemplified above for $R^1$.

The $C_{1-6}$ haloalkyl group represented by $R^4$ includes the $C_{1-6}$ haloalkyl groups exemplified above for $R^2$. In particular, trifluoromethyl is preferable.

The halogen atom represented by $X^2$ includes fluorine, chlorine, bromine and iodine. In particular, chlorine is preferable.

The $C_{1-6}$ alkyl group represented by $R^5$ and $R^6$ includes the $C_{1-6}$ alkyl groups exemplified above for $R^1$. In particular, methyl is preferable.

The cyclic amino group formed by $R^5$ and $R^6$ together with their adjacent nitrogen atom includes e.g. cyclic amino groups such as 1-pyrrolidino, piperidino, morpholino and 4-methyl-1-piperazino. In particular, morpholino is preferable.

The reaction schemes in the present invention are as follows.

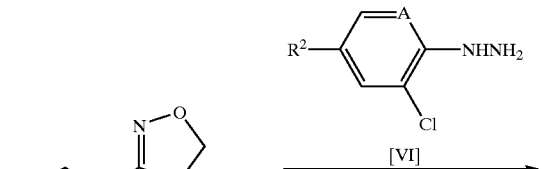

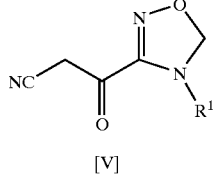

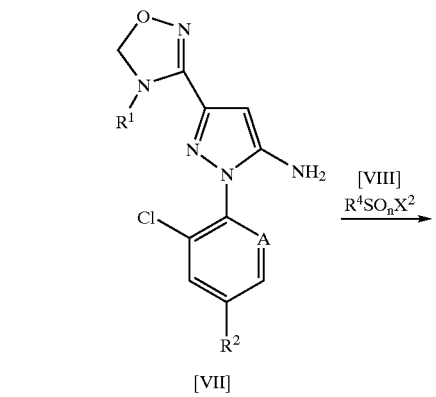

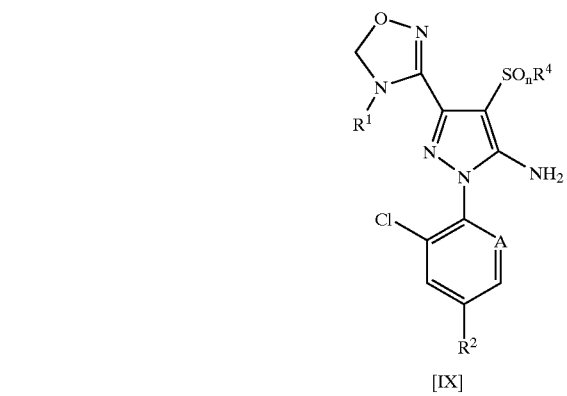

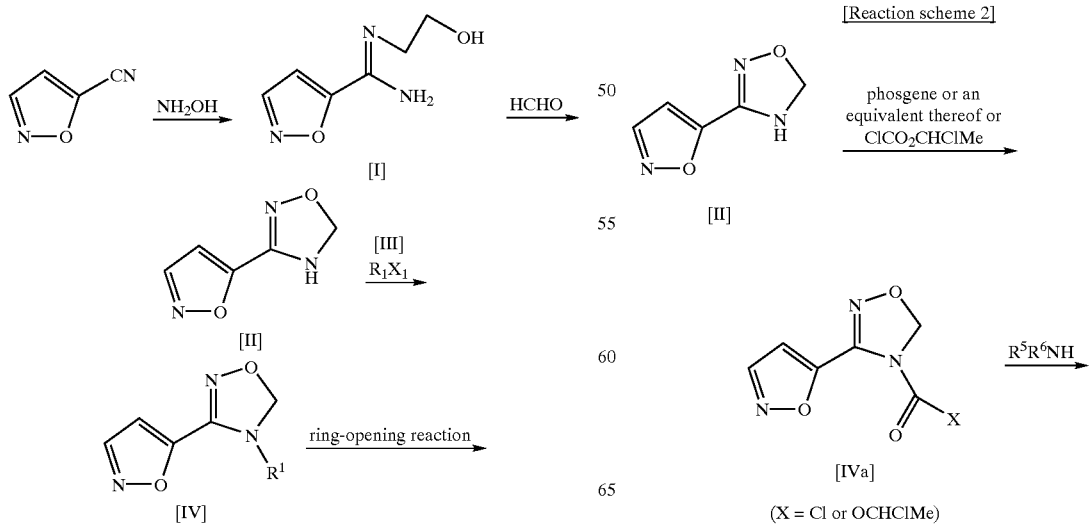

-continued

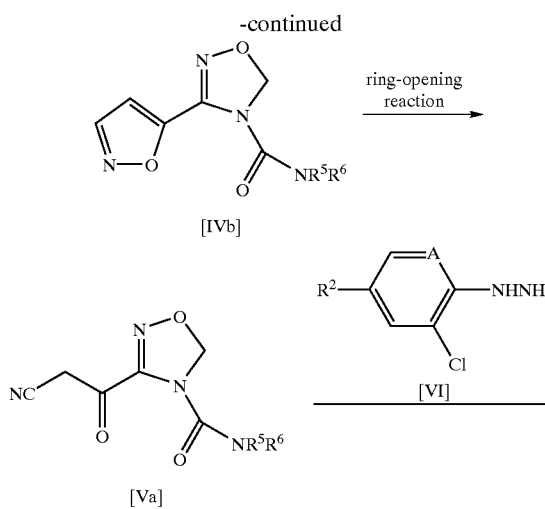

[IVb]

[Va]

[VIIa]

[IXa]

In the reaction scheme 1, 5-cyanoisoxazole is reacted with hydroxylamine or a salt thereof, whereby isoxazole-5-carboxamide oxime represented by compound [I] or a salt thereof can be produced.

The salt of compound [I] usually includes salts with acids, and the acids include e.g. inorganic protonic acids such as hydrochloric acid, hydrobromic acid, hydriodic acid, phosphoric acid and sulfuric acid, organic protonic acids such as formic acid, acetic acid, tartaric acid, malic acid, citric acid, oxalic acid, succinic acid, benzoic acid, trifluoroacetic acid and p-toluene sulfonic acid, and Lewis acids such as aluminum chloride, ferric chloride, zinc chloride, titanium tetrachloride and boron trifluoride.

5-Cyanoisoxazole used as the starting material is a known compound (Gazz. chim. ital. 62, 436 (1932), bp. 168° C.). This starting compound can be isolated for use, but it can also be generated by dehydration reaction of its precursor 5-isoxazole carboxamide, and subjected directly or after isolation to the subsequent reaction.

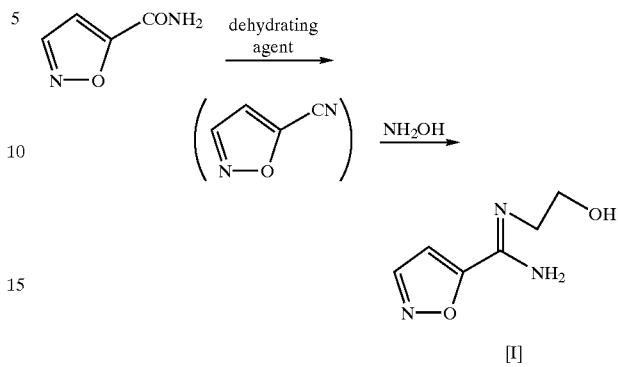

[I]

The dehydrating agent in the reaction scheme includes known dehydrating agents such as phosphorus pentaoxide, phosphorus pentachloride, phosphorus oxychloride, thionyl chloride, trifluoroacetic anhydride, phosgene and dicyclohexyl carbodiimide. The dehydrating reaction can be conducted by a method described in e.g. "Organic Functional Group Preparations Second Edition" Academic Press, Vol. 1, Chapter 17 (1983) or by an analogous method.

Compound [I] occurs as geometrical isomers described below, and the present invention encompasses all the isomers and mixtures thereof.

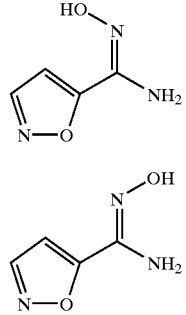

[I-E]

[I-Z]

Hydroxylamine used in this reaction or a salt thereof can be used in any form, and for example, it can be subjected to the reaction in the form of hydrochloride, sulfate or an aqueous solution.

In this reaction, the amount of hydroxylamine or a salt thereof is not particularly limited, and hydroxylamine or a salt thereof also serving as a solvent can be used in large excess, preferably in an amount of about 0.8 to 5 equivalents.

For the purpose of promoting the reaction or decreasing byproducts, a base is coexistent or allowed to act before and after the reaction, whereby good results may be obtained. The base includes e.g. alkali metal alcoholates such as sodium ethylate, sodium methylate and potassium tert-butoxide, organic bases such as ammonia, triethylamine, diisopropyl ethylamine, pyridine, 4-dimethyl aminopyridine and N,N-dimethyl aniline, and inorganic bases such as potassium carbonate, sodium carbonate, sodium hydroxide, potassium hydroxide, sodium bicarbonate, potassium bicarbonate and sodium hydride. The amount of the base used is not particularly limited insofar as the reaction is not adversely affected, and the base also serving as a solvent can be used in large excess.

This reaction can be carried out in a suitable solvent. The solvent is not particularly limited unless it reacts with the reaction substrate, the reaction reagent and the product to give byproducts, and the solvent is desirably the one dissolving both the reaction substrate and the reaction reagent. Such solvent includes e.g. aliphatic hydrocarbons such as pentane, hexane, heptane and petroleum ether, aromatic hydrocarbons such as benzene, toluene and xylene, esters such as methyl acetate, ethyl acetate, ethyl formate and ethyl propionate, alcohols such as methanol, ethanol, propanol, isopropanol and butanol, ketones such as acetone and methyl ethyl ketone, ethers such as diethyl ether, dipropyl ether, diisopropyl ether, dibutyl ether, tetrahydrofuran and dioxane, nitriles such as acetonitrile and propionitrile, acid amides such as dimethyl formamide and dimethyl acetamide, sulfoxides such as dimethyl sulfoxide, sulfones such as sulfolane, phosphoric acid amides such as hexamethyl phosphoramide, halogenated hydrocarbons such as dichloromethane, chloroform, 1,2-dichloroethane and carbon tetrachloride, and aromatic amines such as pyridine, picoline, lutidine and quinoline, as well as mixed solvents thereof, water, and mixed solvents thereof with water.

The reaction temperature is usually −30 to 150° C., preferably −10 to 80° C. The reaction time is usually 0.1 to 72 hours, more preferably about 0.1 to 24 hours.

The resultant compound [I] or a salt thereof can be subjected as the starting material in the subsequent reaction in the form of the reaction mixture or after separation and purification by a means known per se, for example, concentration, concentration under reduced pressure, conversion of liquid properties, transfer to other solvent, solvent extraction, distillation, crystallization, recrystallization and chromatography.

In the reaction formula 1, isoxazole-5-carboxamide oxime represented by compound [I] or a salt thereof is reacted with formaldehyde or an equivalent thereof, whereby 3-(5-isoxazolyl)-$\Delta^2$-1,2,4-oxadiazoline represented by compound [II] or a salt thereof can be produced.

The salt of compound [II] includes salts with the acids exemplified above in compound [I].

Usually, compound [II] occurs as tautomers described below, and the present invention encompasses all such tautomers and mixtures thereof.

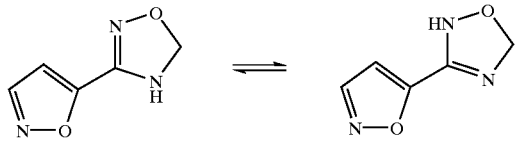

Formaldehyde used in the present invention or an equivalent thereof includes formaldehyde, formalin (aqueous solution of formaldehyde), para-formaldehyde and dimethoxymethane. The amount thereof is not particularly limited, and also serving as a solvent, it can also be used in large amount, preferably in an amount of 0.8 to 15 equivalents.

For the purpose of promoting the reaction or decreasing byproducts, an acid is coexistent or allowed to act before and after the reaction, whereby good results may be obtained. Such acid catalysts include e.g. inorganic protonic acids such as hydrochloric acid, hydrobromic acid, hydriodic acid, phosphoric acid and sulfuric acid, organic protonic acids such as formic acid, acetic acid, tartaric acid, malic acid, citric acid, oxalic acid, succinic acid, benzoic acid, trifluoacetic acid and p-toluene sulfonic acid, and Lewis acids such as aluminum chloride, ferric chloride, zinc chloride, titanium tetrachloride and boron trifluoride. The amount of the acid catalyst used in the reaction is not particularly limited insofar as the reaction is not adversely affected, and the acid catalyst also serving as a solvent can be used in large excess. The acid is particularly preferably acetic acid or p-toluene sulfonic acid.

This reaction can be carried out in a suitable solvent. The solvent is not particularly limited unless it reacts with the reaction substrate, the reaction reagent and the product to give byproducts, and the solvent is desirably the one dissolving both the reaction substrate and the reaction reagent, and for example, the solvent described above in producing compound [I] is similarly used.

The reaction temperature is usually −30 to 200° C., preferably 0 to 150° C. The reaction time is generally 0.1 to 96 hours, more preferably about 0.1 to 48 hours.

The resultant compound [II] or a salt thereof can be subjected as the starting material in the subsequent reaction in the form of the reaction mixture or after separation and purification by a means known per se, for example, concentration, concentration under reduced pressure, conversion of liquid properties, transfer to other solvent, solvent extraction, distillation, is crystallization, recrystallization and chromatography.

In the reaction scheme 1, 3-(5-isoxazolyl)-$\Delta^2$-1,2,4-oxadiazoline represented by compound [II] or a salt thereof is reacted with compound [III], whereby compound [IV] or a salt thereof can be produced.

The salt of compound [IV] includes salts with the acids exemplified above for compound [I].

Compound [III] or an equivalent thereof includes e.g. phosgene, trichloromethyl chloroformate (diphosgene), bis-trichloromethyl carbonate (triphosgene), 1-chloroethyl chloroformate, and an acylating agent represented by $R^1COL$ [$R^1$ has the same meaning as defined above, and L represents a halogen atom (for example, fluorine, chlorine, bromine, iodine), acyloxy group ($C_{1-10}$ acyloxy group, for example, formyloxy group; $C_{1-6}$ alkyl-carbonyloxy group optionally substituted with 1 to 3 halogen atoms, such as acetoxy group, propionyloxy group and trifluoroacetoxy group; and $C_{1-6}$ alkoxy-carbonyloxy group such as methoxycarbonyloxy and t-butoxycarbonyloxy]. Compound [III] is a known compound or can be produced easily from a known compound.

Compound [III] used in this reaction or an equivalent thereof may have formed a salt. Such salts include e.g. salts with inorganic protonic acids such as hydrochloric acid, hydrobromic acid, hydriodic acid, phosphoric acid and sulfuric acid, salts with organic protonic acids such as formic acid, acetic acid, tartaric acid, malic acid, citric acid, oxalic acid, succinic acid, benzoic acid, trifluoacetic acid and p-toluene sulfonic acid, and salts with Lewis acids such as aluminum chloride, ferric chloride, zinc chloride, titanium tetrachloride and boron trifluoride.

The amount of compound [III] used in this reaction or an equivalent thereof is not particularly limited insofar as the reaction is adversely affected, and the amount thereof is preferably 0.8 to 5 equivalents.

For the purpose of promoting the reaction with decreasing byproducts, a base is coexistent or allowed to act before and after the reaction, whereby good results may be obtained. As the base, the base described above in producing compound

[I] is similarly used. The amount of the base used is not particularly limited insofar as the reaction is not adversely affected, and the base also serving as a solvent can be used in large excess.

This reaction can be carried out in a suitable solvent. The solvent is not particularly limited unless it reacts with the reaction substrate, the reaction reagent and the product to give byproducts, and the solvent is desirably the one dissolving both the reaction substrate and the reaction reagent, and for example, the solvent described above in producing compound [I] is similarly used.

The reaction temperature is usually about −50 to 200° C., more preferably −30 to 150° C. The reaction time is generally 0.1 to 96 hours, more preferably about 0.1 to 48 hours.

The resultant compound [IV] or a salt thereof can be subjected as the starting material in the subsequent reaction in the form of the reaction mixture or after separation and purification by a means known per se, for example, concentration, concentration under reduced pressure, conversion of liquid properties, transfer to other solvent, solvent extraction, distillation, crystallization, recrystallization and chromatography.

In the reaction scheme 1, the compound [IV] or a salt thereof can be subjected if necessary to the ring-opening reaction of the isoxazole ring, to produce compound [V] or a salt thereof. The salt of compound [V] includes salts with the acids exemplified above for compound [I].

Usually, compound [V] has tautomers described below, and the present invention encompasses all such tautomers and mixtures thereof.

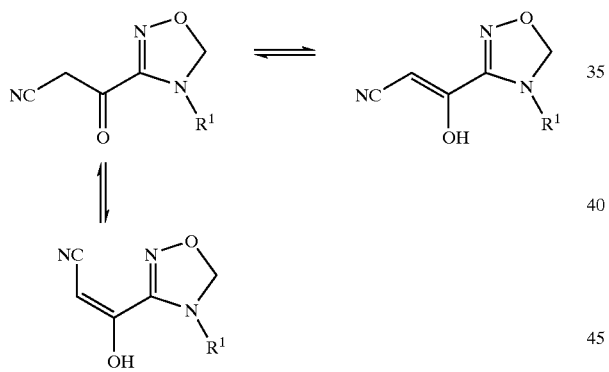

As the base used in this reaction, for example, the base described above in producing compound [I] is similarly used. The amount of the base is not particularly limited insofar as the reaction is not adversely affected, and the base also serving as a solvent can be used in large excess, preferably in an amount of 0.8 to 5 equivalents.

This reaction can be carried out using a suitable solvent. Such solvent is not particularly limited unless it reacts with the reaction substrate, the reaction reagent and the product to give byproducts, and the solvent is desirably the one dissolving the reaction substrate and the reaction reagent, and for example, the solvent enumerated above in production of compound [I] is similarly used.

The reaction temperature is usually −50 to 200° C., preferably −30 to 150° C. The reaction time is usually 0.1 to 96 hours, more preferably about 0.1 to 48 hours.

The resultant compound [V] or a salt thereof can be subjected as the starting material in the subsequent reaction in the form of the reaction mixture or after separation and purification by a means known per se, for example, concentration, concentration under reduced pressure, conversion of liquid properties, transfer to other solvent, solvent extraction, distillation, crystallization, recrystallization and chromatography.

In the reaction scheme 1, compound [V] or a salt thereof is reacted with a hydrazine derivative represented by compound [VI] or a salt thereof, whereby compound [VII] or a salt thereof can be synthesized. The salts of compounds [VI] and [VII] include the acids exemplified above for compound [I]. Compound [VI] is, for example, 2,6-dichloro-4-trifluoromethyl phenyl hydrazine, and it is a known compound or can be produced easily from a known compound. This reaction proceeds via hydrazone derivative [XI] as intermediate as shown in the reaction scheme below, and the intermediate [XI] can also be generally isolated. Subsequently, a base is allowed to act on [XI] formed as intermediate, thus converting it into compound [VII] or a salt thereof.

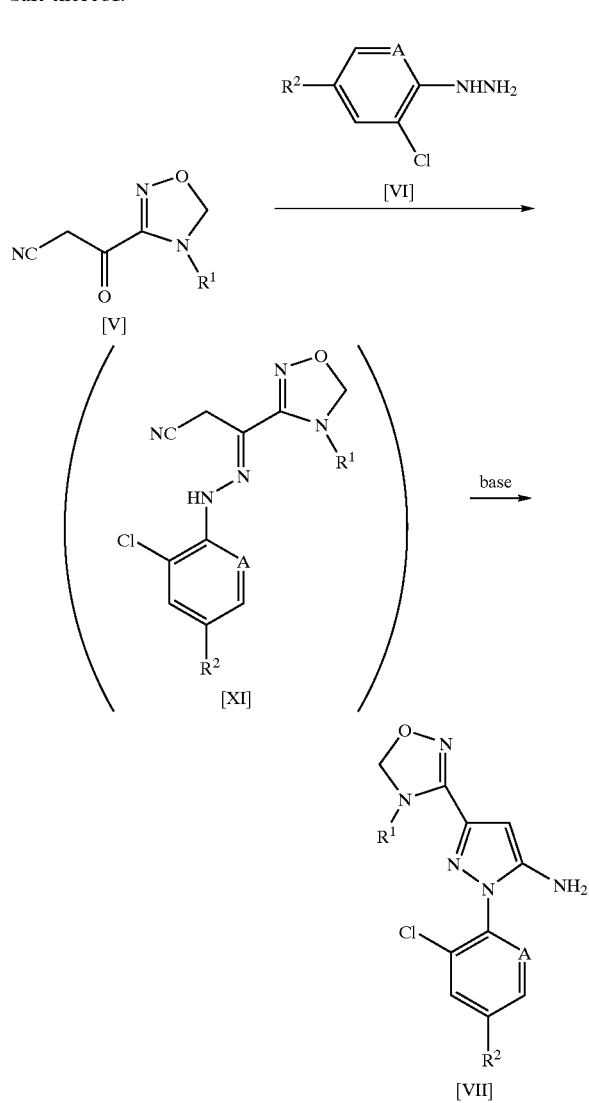

In the reaction of compound [V] or a salt thereof with compound [VI], the reaction may be promoted in the presence of a suitable acid catalyst if necessary. As the acid catalyst, the acid described above in producing compound [II] is similarly used. The amount of the acid used is not particularly limited insofar as the reaction is not adversely affected, and the acid also serving as a solvent can be used in large excess.

As the base used in conversion of the intermediate [XI] thorough ring closure into compound [VII] or a salt thereof, the base described above in producing compound [I] is similarly used. The amount of the base used is not particularly limited insofar as the reaction is adversely affected, and the base also serving as a solvent can be used in large excess, preferably in an amount of 0.8 to 5 equivalents.

When the reaction of converting the compound [IV] into compound [V] is followed by this reaction, good results may be obtained.

This reaction can be carried out in a suitable solvent. The solvent is not particularly limited unless it reacts with the reaction substrate, the reaction reagent and the product to give byproducts, and the solvent is desirably the one dissolving both the reaction substrate and the reaction reagent, and for example, the solvent described above in producing compound [I] is similarly used.

The reaction temperature is usually −50 to 200° C., preferably −30 to 150° C. The reaction time is usually 0.1 to 96 hours, more preferably about 0.1 to 48 hours.

The resultant compound [VII] or a salt thereof can be subjected as the starting material in the subsequent reaction in the form of the reaction mixture or after separation and purification by a means known per se, for example, concentration, concentration under reduced pressure, conversion of liquid properties, transfer to other solvent, solvent extraction, distillation, crystallization, recrystallization and chromatography.

In the reaction scheme 1, the compound [VII] or a salt thereof can be reacted with compound [VIII] to produce compound [IX] or a salt thereof. The salt of compound [IX] includes salts with the acids exemplified above for compound [I]. The compound [VIII] is, for example, trifluoromethane sulphenyl chloride or trifluoromethane sulfinyl chloride, and it is a known compound or can be easily produced from a known compound.

The amount of compound [VIII] used in this reaction is not particularly limited, and is preferably about 0.8 to 5 equivalents.

For the purpose of promoting the reaction while lessening byproducts, an organic base salt is coexistent, whereby good results may be obtained. The organic base salt includes e.g. dimethylamine hydrochloride, dimethylamine-p-toluene sulfonate, triethylamine hydrochloride, pyridine hydrochloride, and pyridine-p-toluene sulfonate. Further, a suitable acid or base catalyst is allowed to coexist, whereby good results may be obtained. As the acid or base catalyst, the base described above in producing compound [I] or the acid described above in producing compound [II] is used. The amount of the organic base salt, acid and base used as the catalyst is not particularly limited insofar as the reaction is not adversely affected, and such salt, acid and base also serving as a solvent can be used in large excess, preferably in an amount of 0.8 to 5 equivalents.

This reaction can be carried out in a suitable solvent. The solvent is not particularly limited unless it reacts with the reaction substrate, the reaction reagent and the product to give byproducts, and the solvent is desirably the one dissolving both the reaction substrate and the reaction reagent, and for example, the solvent described above in producing compound [I] is similarly used.

The reaction temperature is usually about −50 to 200° C., preferably −30 to 150° C. The reaction time is generally 0.1 to 96 hours, more preferably about 0.1 to 48 hours.

The resultant compound [IX] or a salt thereof can be subjected as the starting material in the subsequent reaction in the form of the reaction mixture or after separation and purification by a means known per se, for example, concentration, concentration under reduced pressure, conversion of liquid properties, transfer to other solvent, solvent extraction, distillation, crystallization, recrystallization and chromatography.

The reaction scheme 2, when compound [IV] in the reaction scheme 1 represents compound [IV$_a$], shows the reaction of producing compounds [V$_a$], [VII$_a$] and [IX$_a$] (included in compounds [V], [VII] and [IX], respectively) via compound [IV$_b$], and the reaction scheme 2 is included in the reaction scheme 1.

In the reaction scheme 2, compound [II] or a salt thereof is reacted with phosgene or an equivalent thereof or 1-chloroethyl chlorocarbonate, whereby compound [IV$_a$] or a salt thereof can be produced. Compound [IV$_a$] or a salt thereof can be generally isolated, but when compound [IV$_a$] is instable as in reaction with phosgene or an equivalent thereof (when X=Cl), compound [IV$_a$] is subjected desirably without isolation to the subsequent reaction. The salt of compound [IV$_a$] includes the salts described above for compound [IV].

As the phosgene used in this reaction or an equivalent thereof, phosgene, trichloromethyl chloroformate (diphosgene), bistrichloromethyl carbonate (triphosgene) etc are used. The amount thereof is not particularly limited, and is preferably 0.3 to 5 equivalents.

For the purpose of promoting the reaction with decreasing byproducts, a base is coexistent or allowed to act before and after the reaction, whereby good results may be obtained. As the base, the base described above in producing compound [I] is similarly used. The amount of the base used is not particularly limited insofar as the reaction is not adversely affected, and is preferably 0.3 to 5 equivalents.

This reaction can be carried out in a suitable solvent. The solvent is not particularly limited unless it reacts with the reaction substrate, the reaction reagent and the product to give byproducts, and the solvent is desirably the one dissolving both the reaction substrate and the reaction reagent, and for example, the solvent described above in producing compound [I] is similarly used.

The reaction temperature is usually about −50 to 200° C., preferably −30 to 150° C. The reaction time is generally 0.1 to 96 hours, more preferably about 0.1 to 48 hours.

The resultant compound [IV$_a$] or a salt thereof can be subjected as the starting material in the subsequent reaction in the form of the reaction mixture or after separation and purification by a means known per se, for example, concentration, concentration under reduced pressure, conversion of liquid properties, transfer to other solvent, solvent extraction, distillation, crystallization, recrystallization and chromatography.

In the reaction scheme 2, compound [IV$_a$] or a salt thereof is reacted with an amine represented by $R^5R^6NH$, whereby compound [IV$_b$] or a salt thereof can be produced.

The amine represented by $R^5R^6NH$ is a known compound such as dimethylamine, diethylamine, di-n-propylamine, dibutylamine, di-n-butylamine, methyl ethylamine, ethyl n-propylamine, pyrrolidine, piperidine, morpholine or N-methyl piperazine, or can be easily produced from the known compound.

The amount of the amine used in this reaction is not particularly limited, and is preferably about 0.8 to 5 equivalents.

This reaction can be carried out in a suitable solvent. The solvent is not particularly limited unless it reacts with the reaction substrate, the reaction reagent and the product to give byproducts, and the solvent is desirably the one dissolving both the reaction substrate and the reaction reagent, and for example, the solvent described above in producing compound [I] is similarly used.

The reaction temperature is usually about −50 to 200° C., preferably −30 to 150° C. The reaction time is generally 0.1 to 72 hours, more preferably about 0.1 to 24 hours.

The resultant compound $[Vb_b]$ or a salt thereof can be subjected as the starting material in the subsequent reaction in the form of the reaction mixture or after separation and purification by a means known per se, for example, concentration, concentration under reduced pressure, conversion of liquid properties, transfer to other solvent, solvent extraction, distillation, crystallization, recrystallization and chromatography.

The process of conversion of compound $[IV_b] \rightarrow [V_a] \rightarrow [VII_a] \rightarrow [IX_a]$ in the reaction scheme 2 can be carried out in accordance with the process of conversion of compound $[IV] \rightarrow [V] \rightarrow [VII] \rightarrow [IX]$ in the reaction scheme 1.

The compounds [IX] and $[IX_a]$ and salts thereof produced according to the process of the present invention are effective for control of hygienically harmful insects, animal and plant parasitic insects, and exhibit strong insecticidal action by application to animal and plants where the parasitic insects live. The chemical damage to plants by the compound [I] of the present invention and a salt thereof is low, and the toxicity thereof on fishes is also low, so that they have safety and advantageous properties as agents for controlling harmful insects in medical goods, livestock industry, pets, horticulture, and agriculture (Japanese Patent Application No. 11-151959).

For use of the compounds [IX] and $[IX_a]$ or salts thereof as agrochemicals particularly as insecticides, one or more (preferably one to three) of compounds [IX] and $[IX_a]$ or salts thereof as active ingredients are dissolved or suspended in suitable liquid carriers, or mixed with, or absorbed onto, suitable solid carriers depending on the intended use in the form of agrochemical, pharmaceutical or veterinary preparations such as emulsifiable concentrates, liquid preparation, micro-emulsion, flowable concentrates, oil solution, wettable powders, dusts, granules, fine granules, seed-coating, smoking pesticides, tablets, microcapsules, sprays, EW, ointments, and poisonous bait. These agrochemical, pharmaceutical or veterinary preparations can be prepared in a method known per se by adding e.g. an emulsifier, a suspending agent, a spreading agent, a penetrant, a wetting agent, a thickening agent and a stabilizer, if necessary.

The liquid carriers (solvents) used are preferably solvents such as water, alcohols (for example, methyl alcohol, ethyl alcohol, n-propyl alcohol, isopropyl alcohol, ethylene glycol and the like), ketones (for example, acetone, methyl ethyl ketone and the like), ethers (for example, dioxane, tetrahydrofuran, ethylene glycol monomethyl ether, diethylene glycol monomethyl ether, propylene glycol monomethyl ether and the like), aliphatic hydrocarbons (for example, kerosine, kerosene, fuel oil, machine oil and the like), aromatic hydrocarbons (for example, benzene, toluene, xylene, solvent naphtha, methyl naphthalene and the like), halogenated hydrocarbons (for example, dichloromethane, chloroform, carbon tetrachloride and the like), acid amides (for example, N,N-dimethylformamide, N,N-dimethyl acetamide and the like), esters (for example, ethyl acetate, butyl acetate, fatty acid glycerine ester and the like), nitriles (for example, acetonitrile, propionitrile and the like), and these can be used alone or in combination thereof (preferably one to three solvents) in a suitable ratio.

As the solid carriers (diluents and fillers), use is made of plant powders (for example, soybean powder, tobacco powder, wheat flour, wood meal and the like), mineral powders (for example, clays such as kaolin, bentonite and acid clay, talc such as talcum powder and pagodite powder, silica such as diatomaceous earth and mica powder, and the like), alumina, sulfur powder, activated carbon and the like, and one or more (preferably one to three) of these carriers can be mixed in a suitable ratio before use.

Examples of ointment bases suitably added include polyethylene glycol and pectin, higher fatty acid-polyvalent alcohol esters such as monostearic acid glycerine ester, cellulose derivatives such as methyl cellulose, sodium alginate, bentonite, higher alcohols, polyvalent alcohols such as glycerine, vaseline, white vaseline, liquid paraffin, lard, various vegetable oils, lanoline, dehydrated lanoline, hardened oil and one or more (preferably one to three) resins, to which the following surfactants may be added, if necessary.

The surfactants suitably used as an emulsifier, wetting agent, penetrant, dispersant and the like are nonionic and anionic surfactants such as soaps, polyoxyethylene alkyl aryl ethers [for example, Noigen (trade name), E.A142 (trade name) produced by Dai-ichi Kogyo Seiyaku Co., Ltd., and Nonal (trade name) produced by Toho Chemical Co., Ltd.], alkyl sulfates [for example, Emal 10 (trade name), Emal 40 (trade name) produced by Kao Corporation], alkyl sulfonates [for example, Neogen (trade name), Neogen T (trade name) produced by Dai-ichi Kogyo Seiyaku Co., Ltd., and Neopelex produced by Kao Corporation], polyethylene glycol ethers [for example, Nonipol 85 (trade name), Nonipol 100 (trade name), Nonipol 160 (trade name) produced by Sanyo Chemical Industries, Ltd.], polyvalent alcohol esters [for example, Tween 20 (trade name), Tween 80 (trade name) produced by Kao Corporation]. Further, compound [I] or a salt thereof can be compounded suitably with other insecticides (pyrethroid insecticides, organo phosphorus insecticides, carbamate insecticides, neonicotinoide insecticides, naturally occurring insecticides and the like), acaricides, nematicides, herbicides, plant hormones, plant growth regulators, fungicides (for example, copper fungicide, organic chloride fungicide, organic sulfur fungicide, phenolic fungicide and the like), synergistic agents, attractants, repellents, pigments, fertilizers and the like In the agrochemical composition (insecticide) comprising the compounds produced according to the process of the present invention, the content of compounds [IX] and $[IX_a]$ or salts thereof is usually about 0.1 to 80% by weight, preferably about 1 to 20% by weight, based on the total weight of the composition. Specifically, when these active ingredients are used in an emulsifier, liquid, wettable powder (for example, a granular wettable powder) and the like, the content thereof is usually about 1 to 80% by weight, preferably about 1 to 20% by weight. When these active ingredients are used in oil, powder and the like, the content thereof is usually about 0.1 to 50% by weight, preferably about 0.1 to 20% by weight. When the active ingredients are used in powder, the content thereof is usually about 5 to 50% by weight, preferably about 1 to 20% by weight.

The amount of other agricultural active ingredients (for example, insecticides, herbicides, acaricides and/or fungicides) incorporated into the agrochemical composition of the present invention is usually in the range of about 1 to 80% by weight, preferably about 1 to 20% by weight, based on the total weight.

The content of additives other than the active ingredients described above is varied depending on the type or content of the agrochemical active ingredients or the form of the formulation, but is usually about 0.001 to 99.9% by weight, preferably about 1 to 99% by weight. Specifically, a surfactant is added in an amount of usually about 1 to 20% by weight, preferably about 1 to 15% by weight, a fluidizing additive in an amount of about 1 to 20% by weight, a carrier in an amount of about 1 to 90% by weight, preferably about 1 to 70% by weight, based on the total weight of the composition. Specifically, when the liquid is produced, it is preferable to add a surfactant in an amount of usually about 1 to 20% by weight, preferably about 1 to 10% by weight and water in an amount of about 20 to 90% by weight. For use, an emulsifier, a hydrating agent (for example, a granular wettable powder) and the like may be sprayed after suitable dilution with e.g. water (for example, about 100- to 5,000-fold).

Typical examples of insecticides, acaricides and fungicides which can be used by mixing with compounds [IX] and [IX$_a$] or salts thereof produced according to the process of the present invention are shown below:

EPN, acephate, isoxathion, isofenphos, isoprocarb, etrimfos, oxydeprofos, quinalphos, cadusafos, chlorethoxyfos, chlorpyrifos, chlorpyrifos-methyl, chlorofenvinphos, salithion, cyanophos, disulfoton, dimethoate, sulprofos, diazinon, thiometon, tetrachlorvinphos, tebupirimfos, trichlorphon, naled, vamidothion, pyraclophos, pyridafenthion, pirimiphos-methyl, fenitrothion, fenthion, phenthoate, fosthiazate, butathiofos, prothiofos, propaphos, profenofos, phosalone, fosthiazate, malathion, methidathion, metolcarb, monocrotophos, BPMC, XMC, alanycarb, ethiofencarb, carbaryl, carbosulfan, carbofuran, xylylcarb, cloethocarb, thiodicarb, triazamate, pirimicarb, fenoxycarb, fenothiocarb, furathiocarb, propoxur, bendiocarb, benfuracarb, methomyl, acrinathrin, imiprothrin, ethofenprox, cycloprothrin, sigma-cypermethrin, cyhalothrin, cyfluthrin, cypermethrin, silafluofen, tefluthrin, deltamethrin, tralomethrin, fenvalerate, fenpropathrin, flucythrinate, fluvalinate, flufenoprox, fluproxyfen, flumethrin, prallethrin, beta-cyfluthrin, benfluthrin, permethrin, acetamiprid, imidacloprid, cartap, thiocyclam, nitenpyram, clotianidine, tefuranidine, AKD-1022, thiomethoxam, bensultap, avermectin, emamectin-benzoate, clofentezine, chlorfluazuron, cyromazine, diafenthiuron, dienochlor, dichlorvos, diflubenzuron, spynosyn, sulfluramid, teflubenzuron, tebufenozide, tebufenpyrad, hydroprene, vaniliprole, pymetrozine, pyridaben, pyriproxyfen, pyrimidifen, fipronil, fenazaquin, fenpyroximate, fluazuron, flucycloxuron, flufenoxuron, buprofezin, hexaflumuron, hexythiazox, milbemycin, metoxadiazone, lufenuron, levamisol, chlorphenapyr, NC-184, etoxazole, IBP, ampropylfos, edifenphos, chlorthiophos, tolclofos-methyl, fosetyl, ipconazole, imazalil, imibenconazole, etaconazole, epoxiconazole, cyproconazole, diniconazole, difenoconazole, tetraconazole, tebuconazole, triadimenol, triadimefon, triticonazole, triforine, bitertanol, viniconazole, fenarimol, fenbuconazole, fluotrimazole, furconazole-cis, flusilazole, flutriafol, bromuconazole, propiconazole, hexaconazole, pefurazoate, penconazole, myclobutanil, metconazole, cabendazin, debacarb, prothiocarb, benomyl, maneb, TPN, isoprothiolane, iprodione, iminoctadine-albesil, iminoctadine-triacetate, ethirimol, etridiazole, oxadixyl, oxycarboxin, oxolinic acid, ofurace, kasugamycin, carboxin, captan, clozylacon, chlobenthiazone, cyprodinil, cyprofuram, diethofencarb, dichlofluanid, diclomezine, zineb, dimethirimol, dimethomorph, dimefluazole, thiabendazole, thiophanate-methyl, thifluzamide, tecloftalam, triazoxide, triclamide, tricyclazole, tridemorph, triflumizole, validamycin A, hymexazol, pyracarbolid, pyrazophos, pyrifenox, pyrimethanil, pyroquilon, ferimzone, fenpiclonil, fenpropidin, fenpropimorph, fthalide, furametpyr, furalaxyl, fluazinam, furcarbanil, fluquinconazole, fludioxonil, flusulfamide, flutolanil, butiobate, prochloraz, procymidone, probenazole, benalaxyl, benodanil, pencycuron, myclozolin, metalaxyl, metsulfovax, methfuroxam, mepanipyrim, mepronil, kresoxim-methyl, azoxystrobin, SSF-126, and carpropamid.

Agrochemical preparations comprising the compounds [IX] and [IX$_a$] or salts thereof produced according to the process of the present invention are advantageous for controlling harmful insects, for example, Hemiptera harmful insects such as *Eurydema rugosum, Scotinophara lurida, Riptortus clavatus, Stephanitis nashi, Laodelphax striatellus, Nilaparvata lugens, Nephotettix cincticeps, Unaspis yanonensis, Aphis glycines, Lipaphis erysimi, Brevicoryne brassicae, Aphis gossypii, Myzus persicae, Aulacorthum solani, Aphis spiraecola, Bemisia tabaci, Trialeurodes vaporariorum, Sogatella furcifera, Empoasca onukii, Pseudococus comstocki, Planococcus citri, Icerya purchasi, Plautia stali, Eysarcoris parvus* and the like, Lepidoptera harmful insects such as *Spodoptera litura, Plutella xylostella, Pieris rapae crucivora,* Chilosupppressalis, *Autographa nigrisigna, Helicoverpa assulta, Pseudaletia separata, Mamestra brassicae, Adoxophyes orana fasciata, Notarcha derogata, Cnaphalocrocis medinalis, Phthorimaea operculella,* Chilopolychrysus, *Typoryza incertulas, Spodoptera exigua, Agrotis segetum,* Agrotisipsilon, Heliothisarmigera, Heliothisvirescens, *Heliothis zea,* Narangaaenescens, *Ostrinia nubilalis, Ostrinia furnacalis, Parnara guttata,* Adoxophyes sp., *Caloptilia theivora, Phyllonorycter ringoneella, Carposina niponensis, Grapholita molesta* and the like, Coleoptera harmful insects such as *Epilachna vigintioctopunc tata,* Aulacophorafemoralis, *Phyllotreta striolata, Oulema oryzae, Echinocnemus squameus, Lissorhoptrus oryzophilus,* Anthonomusgrandis, *Callosobruchus chinensis, Sphenophorus venatus, Popillia japonica, Anomala cuprea,* Diabrotica spp., *Leptinotarsa decemlineata,* Agriotes spp., *Lasioderma serricorne,* Anthrenusverbasci, *Tribolium castaneum,* Lyctusbrunneus, *Anoplophora malasiaca, Tomicus piniperda* and the like, Diptera harmful insects such as *Musca domestica, Culex popiens pallens, Tabanus trigonus, Delia antiqua, Delia platura,* Anophelessinensis, *Agromyza oryzae, Hydrellia griseola, Chlorops oryzae,* Dacuscucurbitae, *Ceratitis capitata, Liriomyza trifolii* and the like, Orthoptera harmful insects such as Locustamigratoria, *Gryllotalpa africana, Oxya yezoensis, Oxya japonica* and the like, Thysanoptera harmful insects such as Thripstabaci, *Thrips parmi, Frankliniella occidentalis, Baliothrips biformis, Scirtothrips dorsalis* and the like, Hymenoptera harmful insects such as Athalia rosae and the like, Blattariae harmful insects such as *Blattella germanica, Periplaneta fuliginosa, Periplaneta japonica, Periplaneta americana* and the like, acaroid harmful insects such as *Tetranychus urticae,* Panonychuscitri, *Tetranychus kanzawai,* Tetranychuscinnabarinus, *Panonychus ulmi,* Aculopspelekassi, *Polyphagotarsonemus latus, Rhizoglyphus echinopus* and the like, nematodes such as *Aphelenchoides besseyi,* Meloidogyneincognita, *Pratylen-* chus penetrans, Nothotylenchus acris and the like, and termites such as Coptotermes formosanus, Reticulitermes speratus, Odontotermes formosanus, Cryptotermes domesticus and the like.

Further, pharmaceutical or veterinary preparations comprising the compounds [IX] and [IX$_a$] or salts thereof produced according to the process of the present invention can be used for keeping public health by expelling arthropods or parasites living in the inside or outside of vertebrates such as humans, cattle, sheep, goats, pigs, chickens, dogs, cats and fishes in the field of treatment of diseases in domestic animals and in livestock industry. For example, the parasites include Ixodes spp., Boophilus spp. (for example, *Boophilus microplus*), Amblyomma spp., Hyalomma spp., Rhipicephalus spp. (for example, *Rhipicephalus appendiculatus*), Haemaphysalis spp., Dermacentor spp., Ornithodoros spp. (for example, *Ornithodoros moubata*), *Dermahyssus gallinae*, Sarcoptes spp. (for example, *Sarcoptes scabiei*), Psoroptes spp., Chorioptes spp., Demodex spp., Eutrombicula spp., Aedes spp., Anopheles spp., Musca spp., Hypoderma spp., Gasterophilus spp., Simulium spp., Triatoma spp., Phthiraptera (for example, Damalinia spp., Linognathus spp.), Ctenocephalides spp., *Monomorium pharaonis*, and nematodes [for example trichostrongyles (for example, *Nippostrongylus brasiliensis, Trichostrongylus axei, Trichostrongylus colubriformis*), trichinae (for example, *Trichinella spiralis*), *Haemonchus contortus*, Nematodirus (for example, *Nematodirus battus*), *Ostertagia circumcincta*, Cooperia spp., *Hymenolepis nana*] and the like.

Agrochemical compositions comprising compounds [IX] and [IX$_a$] or salts thereof produced according to the process of the present invention have excellent insecticidal activity and safety with very low toxicity, and can be used as excellent agrochemical compositions (insecticides). The agrochemical composition of the present invention can be used in the same manner as for conventional agrochemical compositions, and as a result, it can exhibit superior effects to those of the conventional compositions.

For example, the agrochemical composition of the present invention is sprayed in a method known per se into paddy fields, fields, orchards, non-agricultural fields, houses and the like, whereby it is contacted with, or ingested by, the above-described harmful insects growing therein to control them. In another mode, the agrochemical composition of the present invention is administered for example into the inside (into the body) or outside (onto the surface of the above-mentioned vertebrate), whereby arthropods or parasites living in the vertebrate can be expelled.

Specifically, the agrochemical composition of the present invention can be used against the intended harmful insects, for example, by seed treatment, nursery box treatment, planting hole treatment, planting foot treatment, soil treatment, foliar spraying, infusion, poisonous bait, smoking, drenching, or water application in paddy fields. The amount of the composition can be varied in a broad range depending on the application time, application site, application method and the like, but generally the active ingredients (compounds [IX] and [IX$_a$] or salts thereof) are applied in an amount of about 0.3 to 3,000 g, preferably about 50 to 1,000 g, per hectare. Further, when the agrochemical composition is a wettable powder, it may be used after dilution such that the final concentration of the active ingredients is in the range of about 0.1 to 1,000 ppm, preferably about 10 to 500 ppm.

Hereinafter, the present invention is described in more detail by reference to the Examples, which however are not intended to limit the present invention.

Elution in column chromatography in the Examples and Reference Examples was conducted under monitoring with TLC (thin layer chromatography). In monitoring with TLC, Kiesel gel 60F254 (70 to 230 meshes) produced by Merck was used as TLC plate; the same developing solvent as in column chromatography was also used as the solvent in TLC; and a UV detector was used in detection. As the silica gel for column, Kiesel gel 60 (70 to 230 meshes) produced by Merck was also used. NMR spectra showing proton NMR were taken with tetramethyl silane as internal standard by Blukar AC-200P (200 MHz) type spectrometer, and all δ values were expressed in ppm. When a mixed solvent was used as the developing solvent, a numerical value in parentheses is indicative of a mixing ratio by volume of each solvent. Abbreviations in the Examples and Reference Examples have the following meaning: Me, methyl group; Et, ethyl group; Ph, phenyl group; Pr-n (or n-Pr), n-propyl; Pr-i (or i-Pr or iPr), isopropyl; Bu-n (or n-Bu), n-butyl; Bu-i (or i-Bu), isobutyl; Bu-s (or s-Bu), sec-butyl; Bu-t (or t-Bu), tert-butyl; s, singlet; br, broad; brs, broad singlet; d, doublet; t, triplet; q, quartet;, qu, quintet; sep, septet; m, multiplet; dd, double doublet; dt, double triplet; J, coupling constant; Hz, hertz; %, weight-%; m.p., melting point, and "room temperature" means about 15 to 25° C..

EXAMPLE 1

Isoxazole-5-carboxamide oxime

To a solution of 2.80 g (25.0 mmol) of 5-isoxazole carboxamide in 30 ml of dimethylformamide was added dropwise 2.80 ml (30.3 mmol) of phosphorus oxychloride under ice-cooling. After this addition, the mixture was raised to room temperature and stirred for 1 hour. The reaction mixture was poured into 100 ml of ice-water and extracted with 100 ml of ethyl acetate. The aqueous layer was subjected to salting-out and extracted twice with 100 ml of ethyl acetate. The ethyl acetate extracts were combined, dried over magnesium sulfate anhydride and concentrated to give 5-cyanoisoxazole as pale yellow oily matter. This product was dissolved by adding 30 ml of methanol, then 2.32 g (32.5 mmol) of hydroxylamine hydrochloride was added, and 4.55 ml (32.5 mmol) of triethylamine was further added, and the mixture was stirred at room temperature for 18 hours. After methanol was distilled off under reduced pressure, 100 ml of aqueous saturated saline was added, and the reaction mixture was extracted 3 times with 100 ml of ethyl acetate. The ethyl acetate extracts were combined, dried over magnesium sulfate anhydride and concentrated to give colorless crystals. Recrystallization thereof from chloroform gave 2.90 g (22.8 mmol) of the title compound as colorless crystals.

Yield 91%.

mp. 146–148° C.

NMR(DMSO-d$_6$, δ) 6.07(2H, br), 6.76(1H, d, J=1.9 Hz), 8.59(1H, d, J=1.9 Hz), 10.18(1H, brs).

EXAMPLE 2

3-(5-Isoxazolyl)-Δ$^2$-1,2,4-oxadiazoline

To a solution of 1.76 g (13.8 mmol) of isoxazole-5-carboxamide oxime in 30 ml of acetonitrile were added 5.2 ml (69.4 mmol) of 37% aqueous formalin and 0.5 ml of acetic acid, and the mixture was heated under reflux for 30 hours. The acetonitrile was distilled off under reduced pressure, and 50 ml of ethyl acetate was added, followed by washing twice with 20 ml of aqueous saturated saline. The ethyl acetate extract was dried over magnesium sulfate anhydride and concentrated to give yellow oily matter. To the oil were added 20 ml of acetonitrile, and then added 1.0 ml (13.4 mmol) of 25% ammonia water. The mixture was stirred at room temperature for 20 minutes, the solvent was distilled off, and 50 ml of ethyl acetate was added, followed by washing with 20 ml of aqueous saturated saline. The reaction mixture was dried over magnesium sulfate anhydride and concentrated to give yellow crystals. After purification by silica gel column chromatography (ethyl acetate:chloroform=1:1), the resultant crystals were washed with a mixed solvent of n-hexane and chloroform (1:1), to give 1.37 g (9.84 mmol) of the title compound as colorless crystals.

Yield 71%.

mp. 128–129° C.

NMR(DMSO-$d_6$, δ) 5.38(2H, d, J=2.8 Hz), 6.97(1H, d, J=1.9 Hz), 7.74(1H, br), 8.73(1H, d, J=1.9 Hz).

EXAMPLE 3

4-Dimethylcarbamoyl-3-(5-isoxazolyl)-$\Delta^2$-1,2,4-oxadiazoline (Method of Using Triphosgene)

To a solution of 2.89 g (9.74 mmol) of bis(trichloromethyl)carbonate (triphosgene) in 5 ml of tetrahydrofuran was added dropwise 3.50 g (44.2 mmol) of pyridine under ice-cooling. After stirring for 30 minutes under cooling on ice, a solution of 3.37 g (24.2 mmol) of 3-(5-isoxazolyl)-$\Delta^2$-1,2,4-oxadiazoline in 40 ml of tetrahydrofuran was added dropwise thereto under ice-cooling. After the mixture was stirred for 1 hour under ice-cooling, 7.7 ml (73.4 mmol) of 50% aqueous dimethylamine was added dropwise, and the resultant mixture was stirred for 30 minutes, raised to room temperature and stirred for 16 hours. To the mixture were added 30 ml of water and 30 ml of aqueous saturated saline, and the reaction mixture was extracted with 50 ml of ethyl acetate. The ethyl acetate layer was washed twice with 30 ml of aqueous saturated saline and dried over magnesium sulfate anhydride, and the solvent was distilled off, whereby brown oily matter was obtained. After purification by silica gel column chromatography (acetone:n-hexane=1:1), the resultant crystals were washed with a mixed solvent of n-hexane and chloroform (10:1), to give 4.03 g (19.2 mmol) of the title compound as colorless crystals.

Yield 79%.

mp. 93–95° C.

NMR(CDCl$_3$, δ) 3.01(6H, s), 5.58(2H, s), 6.80(1H, d, J=1.9 Hz), 8.33(1H, d, J=1.9 Hz).

EXAMPLE 4

3-Cyanoacetyl-4-dimethylcarbamoyl-$\Delta^2$-1,2,4-oxadiazoline

To 840 mg (4.0 mmol) of 4-dimethylcarbamoyl-3-(5-isoxazolyl)-$\Delta^2$-1,2,4-oxadiazoline were added 2 ml of water and 2.16 g (5.4 mmol) of 10% aqueous sodium hydroxide, and the mixture was stirred at room temperature for 30 minutes. The mixture was adjusted to pH 1 by adding about 5 ml of 1.2 N hydrochloric acid, then extracted once with 30 ml of ethyl acetate and twice with 20 ml ethyl acetate. The ethyl acetate layers were combined and washed twice with 20 ml of aqueous saturated saline. The solution was dried over magnesium sulfate anhydride and concentrated to give 850 mg (4.0 mmol) of the title compound as brown oily matter.

Yield 100%.

NMR(CDCl$_3$, δ) 2.99(6H, s), 4.09(2H, s), 5.57(2H, s).

EXAMPLE 5

5-Amino-1-(2,6-dichloro-4-trifluoromethylphenyl)-3-(4-dimethylcarbamoyl-$\Delta^2$-1,2,4-oxadiazoline-3-yl)pyrazole To a solution of 370 mg (1.76 mmol) of 3-cyanoacetyl-4-dimethylcarbamoyl-$\Delta^2$-1,2,4-oxadiazoline in 7 ml of methanol was added 289 mg (1.18 mmol) of 2,6-dichloro-4-trifluoromethylphenyl hydrazine. Three drops of 1.2 N hydrochloric acid were added thereto, and the mixture was stirred at room temperature for 3 hours and stirred under reflux for 11 hours. To the mixture was added 50 ml of ethyl acetate, and the resultant mixture was washed twice with 30 ml of aqueous saturated saline. The reaction mixture was dried over magnesium sulfate anhydride and concentrated to give brown oily matter. After purification by silica gel column chromatography (ethyl acetate:n-hexane=2:1), the resultant crystals were washed with a mixed solvent of n-hexane and chloroform (10:1), to give 477 mg (1.09 mmol) of the title compound as colorless crystals.

Yield 62%.

mp. 150–153° C.

NMR(CDCl$_3$, δ) 2.92(6H, s), 3.00(2H, br), 5.50(2H, s), 6.10(1H, s), 7.74–7.75(2H, m).

EXAMPLE 6

5-Amino-1-(2,6-dichloro-4-trifluoromethylphenyl)-3-(4-dimethylcarbamoyl-$\Delta^2$-1,2,4-oxadiazoline-3-yl)pyrazole To a suspension of 500 mg (2.38 mmol) of 4-dimethylcarbamoyl-3-(5-isoxazolyl)-$\Delta^2$-1,2,4-oxadiazoline in 15 ml of methanol was added a solution of 595 mg (2.57 mmol) of 28% sodium methoxide in methanol, and the mixture was stirred at room temperature for 2 hours. To the reaction mixture were added 0.157 ml (2.82 mmol) of conc. sulfuric acid and 583 mg (2.38 mmol) of 2,6-dichloro-4-trifluoromethylphenyl hydrazine, and the mixture was stirred at room temperature for 23 hours. To the mixture was added 0.498 ml (3.57 mmol) of triethylamine, and the mixture was stirred at room temperature for 30 minutes. The reaction mixture was concentrated under reduced pressure, and 50 ml of ethyl acetate was added to the residue which was then washed with aqueous saturated saline and dried over magnesium sulfate anhydride. The reaction mixture was concentrated under reduced pressure, and the resultant crystals were washed with a mixed solvent of n-hexane and ethyl acetate (3:1), to give 720 mg (1.65 mmol) of the title compound as brown crystals.

Yield 69%.

Physical data: see Example 5.

EXAMPLE 7

5-Amino-1-(2,6-dichloro-4-trifluoromethylphenyl)-3-(4-dimethylcarbamoyl-$\Delta^2$-1,2,4-oxadiazoline-3-yl)-4-trifluoromethylsulfinylpyrazole To a solution of 301 mg (0.688 mmol) of 5-amino-1-(2,6-dichloro-4-trifluoromethylphenyl)-3-(4-dimethylcarbamoyl-$\Delta^2$-1,2,4-oxadiazoline-3-yl)pyrazole in 4 ml of 1,2-dichloroethane was added 250 mg (2.16 mmol) of pyridine hydrochloride. To the resultant mixture was added 226 mg (1.48 mmol) of trifluoromethanesulfinylchloride, and the mixture was stirred at room temperature for 4 hours. To the mixture were further added 318 mg (2.75 mmol) of pyridine hydrochloride and 136 mg (0.89 mmol) of trifluoromethanesulfinylchloride. After stirring at room temperature for 22 hours, 40 ml of ethyl acetate was added, and the mixture was washed twice with 20 ml of aqueous saturated saline. After the mixture was dried over magnesium sulfate anhydride, the solvent was distilled off whereby yellowish brown oily matter was obtained. After purification by silica gel column chromatography (ethyl acetate:n-hexane=2:1), the resultant oily matter was washed with a mixed solvent of n-hexane and chloroform (10:1), to give 329 mg (0.594 mmol) of the title compound as colorless crystals.

Yield 86%.

mp. 186–190° C.

NMR(CDCl$_3$, δ) 2.94(6H, s), 5.15(2H, br), 5.46(1H, d, J=1.8 Hz), 5.53(1H, d, J=1.8 Hz), 7.78–7.79(2H, m).

EXAMPLE 8

4-Dimethylcarbamoyl-3-(5-isoxazolyl)-Δ$^2$-1,2,4-oxadiazoline (Method of Using 1-chloroethyl chlorocarbonate)

To a solution of 1.00 g (7.19 mmol) of 3-(5-isoxazolyl)-Δ$^2$-1,2,4-oxadiazoline in 90 ml of acetonitrile was added 1.26 ml (9.03 mmol) of triethylamine. To the mixture was added dropwise 0.69 ml (9.06 mmol) of 1-chloroethyl chlorocarbonate under ice-cooling. After the mixture was stirred for 1 hour under ice-cooling, the acetonitrile was distilled off, 100 ml of water was added thereto, and the reaction mixture was extracted 3 times with 200 ml of ethyl acetate. The ethyl acetate layer was dried over magnesium sulfate anhydride and concentrated, and the resultant residue was dissolved in 40 ml of acetonitrile. To the solution was added dropwise 2.10 ml (22.5 mmol) of 50% aqueous dimethylamine under ice-cooling, the temperature of the mixture was raised to room temperature, and the mixture was stirred for 3 hours. The reaction mixture was poured into 200 ml of 1% hydrochloric acid under ice-cooling and then extracted twice with 200 ml of ethyl acetate. The extract was washed with 300 ml of aqueous saturated saline, dried over magnesium sulfate anhydride and concentrated. The residue was recrystallized by adding a mixed solvent of diisopropyl ether and chloroform (10:1), to give 1.18 g (5.61 mmol) of the title compound as reddish brown crystals.

Yield 78%.

Physical data: see Example 3.

EXAMPLE 9

4-(1-Chloroethoxycarbonyl)-3-(5-isoxazolyl)-Δ$^2$-1,2,4-oxadiazoline

To a solution of 4.20 g (30.0 mmol) of 3-(5-isoxazolyl)-Δ$^2$-1,2,4-oxadiazoline in 200 ml of acetonitrile was added 5.30 ml (37.9 mmol) of triethylamine. To the mixture was added dropwise 2.90 ml (37.9 mmol) of 1-chloroethyl chloroacetate under ice-cooling. The reaction mixture was stirred for 1 hour under ice-cooling and concentrated, and the residue was purified by silica gel column chromatography (ethyl acetate:n-hexane=1:2) to give 5.69 g (23.2 mmol) of the title compound as pale brown oily matter.

Yield 77%.

NMR(CDCl$_3$, δ) 1.72(3H, d, J=5.9 Hz), 5.83–5.87(2H, m), 6.48(1H, q, J=5.9 Hz), 6.90(1H, d, J=1.9 Hz), 8.40(1H, d, J=1.9 Hz).

EXAMPLE 10

4-Dimethylcarbamoyl-3-(5-isoxazolyl)-Δ$^2$-1,2,4-oxadiazoline (Method of Using chloromethyl chlorocarbonate)

To a solution of 1.00 g (7.19 mmol) of 3-(5-isoxazolyl)-Δ$^2$-1,2,4-oxadiazoline in 20 ml of acetonitrile was added 1.26 ml (9.03 mmol) of triethylamine. To the mixture was added dropwise 0.80 ml (9.06 mmol) of chloromethyl chlorocarbonate under ice-cooling. After the reaction mixture was stirred for 1 hour under ice-cooling, insolubles were removed by filtration, and 2.10 ml (22.5 mmol) of 50% aqueous dimethylamine was added dropwise under ice-cooling. The mixture was raised to room temperature, and the reaction mixture was stirred for 3 hours, then poured into 200 ml of 1% hydrochloric acid previously cooled on ice, and extracted twice with 200 ml of ethyl acetate. The extract was washed with 300 ml of aqueous saturated saline, dried over magnesium sulfate anhydride and concentrated. The residue was recrystallized by adding a mixed solvent of diisopropyl ether and chloroform (10:1) to give 0.89 g (4.23 mmol) of the title compound as pale brown crystals.

Yield 59%.

Physical data: see Example 3.

EXAMPLE 11

4-(Chloromethoxycarbonyl)-3-(5-isoxazolyl)-Δ$^2$-1,2,4-oxadiazoline

To a solution of 500 mg (3.60 mmol) of 3-(5-isoxazolyl)-Δ$^2$-1,2,4-oxadiazoline in 45 ml of acetonitrile was added 0.63 ml (4.51 mmol) of triethylamine. To the mixture was added dropwise 0.41 ml (4.51 mmol) of chloromethyl chlorocarbonate under ice-cooling. The reaction mixture was stirred for 1 hour under ice-cooling and then concentrated, and the residue was purified by silica gel column chromatography (ethyl acetate:n-hexane=1:2), to give 569 mg (2.46 mmol) of the title compound as colorless oily matter.

Yield: 68%.

NMR(CDCl$_3$, δ) 5.75(2H, s), 5.84(2H, s), 6.92(1H, d, J=1.9 Hz), 8.40(1H, d, J=1.9 Hz).

EXAMPLE 12

4-Dimethylcarbamoyl-3-(5-isoxazolyl)-Δ$^2$-1,2,4-oxadiazoline (Method of Using phenyl chlorocarbonate)

To a solution of 1.00 g (7.19 mmol) of 3-(5-isoxazolyl)-Δ$^2$-1,2,4-oxadiazoline in 20 ml of acetonitrile was added 1.26 ml (9.03 mmol) of triethylamine. To the mixture was added dropwise 1.14 ml (9.06 mmol) of phenyl chlorocarbonate under ice-cooling. After stirring for 1 hour under ice-cooling, insolubles were removed by filtration, and 2.10 ml (22.5 mmol) of 50% aqueous dimethylamine was added dropwise under ice-cooling. The mixture was raised to room temperature, the mixture was stirred for 3 hours, and the reaction mixture was poured into 200 ml of 1% hydrochloric acid previously cooled on ice, and extracted twice with 200 ml of ethyl acetate. The extract was washed with 300 ml of aqueous saturated saline, dried over magnesium sulfate anhydride and concentrated. The resultant black oily matter was purified by silica gel column chromatography (ethyl acetate), to give 0.45 g (2.14 mmol) of the title compound as pale yellow crystals.

Yield 30%.

Physical data: see Example 3.

EXAMPLE 13

4-(Phenoxycarbonyl)-3-(5-isoxazolyl)-$\Delta^2$-1,2,4-oxadiazoline

To a solution of 500 mg (3.60 mmol) of 3-(5-isoxazolyl)-$\Delta^2$-1,2,4-oxadiazoline in 45 ml of acetonitrile was added 0.63 ml (4.51 mmol) of triethylamine. To the mixture was added dropwise 0.57 ml (4.51 mmol) of phenyl chlorocarbonate under ice-cooling. The reaction mixture was stirred for 1 hour under ice-cooling and concentrated, and the residue was purified by silica gel column chromatography (ethyl acetate:n-hexane=1:2), to give 890 mg (3.43 mmol) of the title compound as colorless oily matter.

Yield: 95%.

NMR(CDCl$_3$, $\delta$) 5.95(2H, s), 6.90(1H, d, J=1.9 Hz), 7.25–7.41(5H, m), 8.35(1H, d, J=1.9 Hz).

EXAMPLE 14

5-Amino-1-(2,6-dichloro-4-trifluoromethylphenyl)-3-(4-dimethylcarbamoyl-$\Delta^2$-1,2,4-oxadiazoline-3-yl)-4-trifluoromethylsulfinylpyrazole To a suspension of 500 mg (1.14 mmol) of 5-amino-1-(2,6-dichloro-4-trifluoromethylphenyl)-3-(4-dimethylcarbamoyl-$\Delta^2$-1,2,4-oxadiazoline-3-yl)pyrazole in 5 ml of toluene was added 373 mg (1.72 mmol) of dimethylamine p-toluene sulfonate. To the mixture was added 227 mg (1.49 mmol) of trifluoromethanesulfinylchloride, and the mixture was stirred at 50° C. for 8 hours. To the reaction mixture was added 50 ml of ethyl acetate and the resultant mixture was then washed with 20 ml of aqueous saturated sodium bicarbonate and then with 20 ml of aqueous saturated saline. The solution was dried over magnesium sulfate anhydride, and the solvent was distilled off, whereby 590 mg (1.07 mmol) of the title compound was obtained as pale brown crystals.

Yield 94%.

Physical data: see Example 7.

EXAMPLE 15

5-Amino-1-(2,6-dichloro-4-trifluoromethylphenyl)-3-(4-dimethylcarbamoyl-$\Delta^2$-1,2,4-oxadiazoline-3-yl)-4-trifluoromethylsulfinylpyrazole To a solution of 500 mg (1.14 mmol) of 5-amino-1-(2,6-dichloro-4-trifluoromethylphenyl)-3-(4-dimethylcarbamoyl-$\Delta^2$-1,2,4-oxadiazoline-3-yl)pyrazole in 5 ml of dichloroethane was added 186 mg (2.29 mmol) of dimethylamine hydrochloride. To the mixture was added 262 mg (1.72 mmol) of trifluoromethanesulfinylchloride, and the mixture was stirred at room temperature for 48 hours. To the reaction mixture was added 50 ml of ethyl acetate and the mixture was then washed with 20 ml of aqueous saturated sodium bicarbonate and then with 20 ml of aqueous saturated saline. The solution was dried over magnesium sulfate anhydride, and the solvent was distilled off, whereby 540 mg (0.98 mmol) of the title compound was obtained as pale brown crystals.

Yield 86%.

Physical data: see Example 7.

EXAMPLE 16

4-Morpholinocarbonyl-3-(5-isoxazolyl)-$\Delta^2$-1,2,4-oxadiazoline

To a solution of 1.68 g (5.72 mmol) of bis(trichloromethyl)carbonate (triphosgene) in 100 ml of tetrahydrofuran was added 2.04 g (25.8 mmol) of pyridine under ice-cooling. The mixture was stirred for 5 minutes under ice-cooling on ice, and a solution of 2.00 g (14.4 mmol) of 3-(5-isoxazolyl)-$\Delta^2$-1,2,4-oxadiazoline in 60 ml of tetrahydrofuran was added dropwise thereto under ice-cooling. After further stirring for 2 hours under ice-cooling, 1.49 g (17.2 mmol) of morpholine was added dropwise under ice-cooling, and the mixture was stirred for 2 hours under ice-cooling. The solvent was distilled off under reduced pressure, 200 ml of aqueous saturated saline was added, and the reaction mixture was extracted twice with 200 ml of ethyl acetate. After the ethyl acetate layer was washed with 300 ml of aqueous saturated saline and dried over magnesium sulfate anhydride, the solvent was distilled off, and the residue was recrystallized from diisopropyl ether and chloroform (5:1), to give 2.10 g (8.33 mmol) of the title compound as colorless crystals.

Yield 58%.

mp. 159–161.5° C.

NMR(CDCl$_3$, $\delta$) 3.48(4H, t, J=4.5 Hz), 3.74(4H, t, J=4.5 Hz), 5.55(2H, s), 6.81(1H, d, J=1.9 Hz), 8.34(H, d, J=1.9 Hz).

EXAMPLE 17

5-Amino-1-(2,6-dichloro-4-trifluoromethylphenyl)-3-(4-morpholinocarbonyl-$\Delta^2$-1,2,4-oxadiazoline-3-yl)pyrazole To a solution of 1 g (3.96 mmol) of 4-morpholinocarbonyl-3-(5-isoxazolyl)-$\Delta^2$-1,2,4-oxadiazoline in 10 ml acetonitrile was added 918 mg (4.76 mmol) of 28% sodium methoxide solution in methanol, and the mixture was stirred for 2.5 hours under ice-cooling. To the mixture were added 0.29 ml (5.44 mmol) of conc. sulfuric acid and a solution of 1.09 g (4.36 mmol) of 2,6-dichloro-4-trifluoromethylphenyl hydrazine in 20 ml of ethanol, and the resultant mixture was stirred at 80° C. for 2 hours. The reaction mixture was raised to room temperature, and 0.90 ml (13.07 mmol) of 25% ammonia water was added, and the mixture was stirred at room temperature for 1 hour. The reaction mixture was concentrated under reduced pressure, and 200 ml of ethyl acetate was added to the residue which was then washed with 100 ml of 10% hydrochloric acid, 100 ml of aqueous saturated saline, 100 ml of saturated aqueous sodium bicarbonate and 100 ml of aqueous saturated saline in this order and dried over magnesium sulfate anhydride. The reaction mixture was concentrated under reduced pressure, and the resulting crystals were washed with a mixed solvent of n-hexane and ethyl acetate (5:1) to give 1.84 g (3.84 mmol) of the title compound as brown crystals.

Yield 97%.

mp. 113–115° C.

NMR(CDCl$_3$, $\delta$) 3.43(4H, t, J=5.2 Hz), 3.64(4H, t, J=5.2 Hz), 5.48(2H, s), 6.09(1H, s), 7.75(2H, m).

EXAMPLE 18

5-Amino-1-(2,6-dichloro-4-trifluoromethylphenyl)-3-(4-morpholinocarbonyl-$\Delta^2$-1,2,4-oxadiazoline-3-yl)-4-trifluoromethylsulfinylpyrazole To a solution of 500 mg (1.04 mmol) of 5-amino-1-(2,6-dichloro-4-trifluoromethylphenyl)-3-(4-morpholinocarbonyl-$\Delta^2$-1,2,4-oxadiazoline-3-yl)pyrazole in 5 ml of acetonitrile was added 122 mg (1.50 mmol) of dimethylamine hydrochloride. To the mixture was added 198 mg (1.30 mmol) of trifluoromethanesulfinylchloride, and the mixture was stirred at room temperature for 24 hours. The solvent was distilled off under reduced pressure, 100 ml of ethyl acetate was added, and the reaction mixture was washed with 100 ml of aqueous saturated sodium bicarbonate and then with 100 ml of aqueous saturated saline. After the reaction mixture was dried over magnesium sulfate anhydride, the solvent was distilled off, and the residue was recrystallized from a mixed solvent of n-hexane and ethyl acetate (5:1), to give 410 mg (0.69 mmol) of the title compound as brown crystals.

Yield 66%.

mp. 177–178.5° C.

NMR(CDCl$_3$, δ) 3.45(4H, t, J=5.6 Hz), 3.65(4H, t, J=5.6 Hz), 5.16(2H, s), 5.45(1H, d, J=1.8 Hz), 5.52(1H, d, J=1.8 Hz), 7.78–7.80(2H, m).

Reference Example 1

5-Amino-1-(2,6-dichloro-4-trifluoromethylphenyl)-3-(4-dimethylcarbamoyl-Δ$^2$-1,2,4-oxadiazoline-3-yl)-4-trifluoromethylsulfinylpyrazole To a solution of 1 g (2.07 mmol) of 5-amino-1-(2,6-dichloro-4-trifluoromethylphenyl)-3-(Δ$^2$-1,2,4-oxadiazoline-3-yl)-4-trifluoromethylsulfinylpyrazole in 10 ml of acetonitrile was added 0.442 mg (2.07 mmol) of diisopropyl-ethylamine, and the mixture was cooled on ice. To the mixture were added 0.233 ml (2.49 mmol) of chloromethyl chlorocarbonate and 5 mg of 4-dimethylaminopyridine, and the mixture was stirred at room temperature for 6 hours. To the reaction mixture was added 3.75 ml (6.22 mmol) of 1.66 M dimethylamine solution in acetonitrile, and the mixture was stirred at room temperature for 1.5 hours. The reaction mixture was concentrated under reduced pressure, and the residue was purified by silica gel column chromatography (ethyl acetate:chloroform=1:1), to give 430 mg (0.78 mmol) of the title compound as yellow solution.

Yield 38%.

Physical data: see Example 7.

Reference Example 2

5-Amino-3-(4-(1-chloroethoxycarbonyl)-Δ$^2$-1,2,4-oxadiazoline-3-yl)-1-(2,6-dichloro-4-trifluoromethyl phenyl)-4-trifluoromethylsulfinylpyrazole To a solution of 5 g (10.4 mmol) of 5-amino-1-(2,6-dichloro-4-trifluoromethylphenyl)-3-(Δ$^2$-1,2,4-oxadiazoline-3-yl)-4-trifluoromethylsulfinylpyrazole in 50 ml acetonitrile was added 1.74 ml (12.5 mmol) of triethylamine, and the mixture was cooled on ice. To the mixture were added 1.34 ml (12.5 mmol) of 1-chloroethyl chlorocarbonate and 10 mg of 4-dimethylaminopyridine, and the mixture was stirred at 60° C. for 24 hours. The reaction mixture was concentrated under reduced pressure, and the residue was purified by silica gel column chromatography (ethyl acetate:n-hexane=1:2), to give 2.7 g (4.83 mmol) of the title compound as yellow amorphous substance.

Yield 47%.

Reference Example 3

5-Amino-1-(2,6-dichloro-4-trifluoromethyl phenyl)-3-(4-dimethylcarbamonyl-Δ$^2$-1,2,4-oxadiazoline-3-yl)-4-trifluoromethylsulfinylpyrazole To a solution of 500 mg (0.895 mmol) of 5-amino-3-(4-(1-chloroethoxycarbonyl)-Δ$^2$-1,2,4-oxadiazoline-3-yl)-1-(2,6-dichloro-4-trifluoromethyl phenyl)-4-trifluoromethylsulfinylpyrazole obtained in Reference Example 2 in 5 ml of acetonitrile was added 2.69 ml (4.46 mmol) of 1.66 M dimethylamine solution in acetonitrile and the mixture was stirred at room temperature for 29 hours. The reaction mixture was concentrated under reduced pressure, and the residue was purified by silica gel column chromatography (ethyl acetate:chloroform=2:1), to give 197 mg (0.358 mmol) of the title compound as yellow solution.

Yield 40%.

Physical data: see Example 7.

As described hereinabove, according to the present invention, there is provided a process which is advantageous for industrial mass production of Δ$^2$-1,2,4-oxadiazoline derivatives having excellent insecticidal effects or a salt thereof in high yield.

What is claimed is:

1. A process for producing isoxazole-5-carboxamide oxime represented by formula [I]:

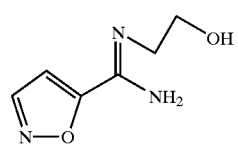

or a salt thereof, which comprises reacting 5-cyanoisoxazole with hydroxylamine or a salt thereof.

2. A process for producing 3-(5-isoxazolyl)-Δ$^2$-1,2,4-oxadiazoline represented by formula [II]:

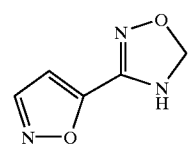

or a salt thereof, which comprises reacting isoxazole-5-carboxamide oxime represented by formula [I]:

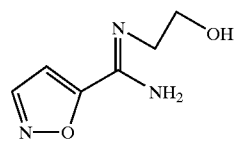

or a salt thereof with formaldehyde or an equivalent thereof.

3. A process for producing a compound represented by formula [IV]:

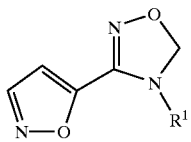

wherein R$^1$ represents an optionally substituted alkyl group, an optionally substituted acyl group or chlorocarbonyl group (ClCO), or a salt thereof, which comprises reacting 3-(5- isoxazolyl)-Δ²-1,2,4-oxadiazoline represented by formula [II]:

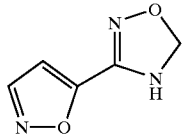

or a salt thereof with a compound represented by formula [III]:

R¹X¹  [III]

wherein X¹ represents a halogen atom, and R¹ is as defined above, or an equivalent thereof or a salt thereof.

4. A process for producing a compound represented by formula [V]:

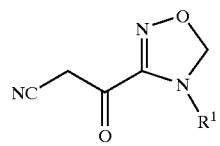

wherein R¹ is as defined in claim 3, or a salt thereof, which comprises subjecting a compound represented by formula [IV]:

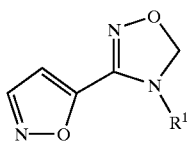

wherein R¹ is as defined in claim 3, or a salt thereof to the ring-opening reaction of the isoxazole ring.

5. A process for producing a compound represented by formula [VII]:

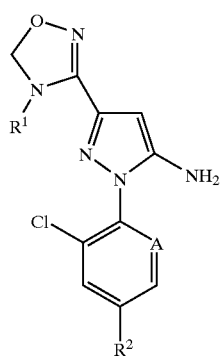

wherein R¹ is as defined in claim 3, and R² represents (1) halogen, (2) $C_{1-6}$ haloalkyl group, (3) $C_{1-6}$ haloalkoxy group or (4) phenyl group optionally substituted with $C_{1-6}$ haloalkyl group, or a salt thereof, which comprises reacting a compound represented by formula [V]:

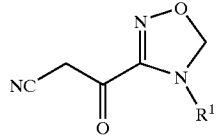

wherein R¹ is as defined in claim 3, or a salt thereof with a compound represented by formula [VI]:

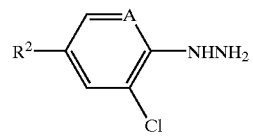

wherein A represents a nitrogen atom or

(wherein R³ represents chlorine atom or cyano group), and the other symbol is as defined above, or a salt thereof.

6. A process for producing a compound represented by formula [IX]:

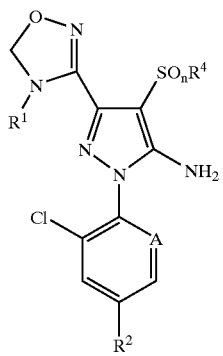

wherein R¹ is as defined in claim 3, R² represents (1) halogen, (2) $C_{1-6}$ haloalkyl group, (3) $C_{1-6}$ haloalkoxy group or (4) phenyl group optionally substituted with $C_{1-6}$ haloalkyl group, A represents a nitrogen atom or

wherein R³ represents chlorine atom or cyano group, and R⁴ represents a $C_{1-6}$ alkyl group or a $C_{1-6}$ haloalkyl group, or a salt thereof, which comprises reacting a compound represented by the formula [VII]:

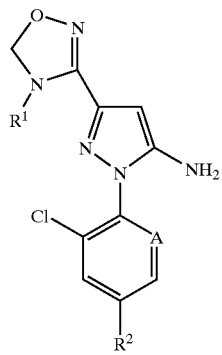

[VII]

wherein $R^1$ is as defined in claim 3, and $R^2$ and A are as defined above, or a salt thereof with a compound represented by formula [VIII]:

[VIII]

wherein $R^4$ is as defined above, n is 0, 1 or 2, and $X^2$ represents a halogen atom.

7. A compound represented by formula [IV]:

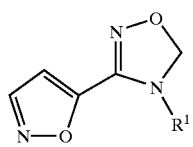

[IV]

wherein $R^1$ are as defined in claim 3, or a salt thereof.

8. A compound represented by formula [V]:

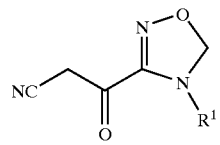

[V]

wherein $R^1$ is as defined in claim 3, or a salt thereof.

9. A compound represented by formula [VII]:

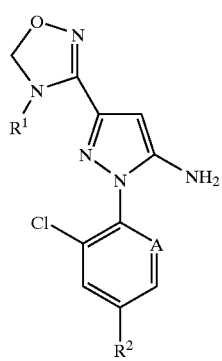

[VII]

wherein $R^1$ is as defined in claim 3, $R^2$ represents (1) halogen, (2) $C_{1-6}$ haloalkyl group, (3) $C_{1-6}$ haloalkoxy group or (4) phenyl group optionally substituted with $C_{1-6}$ haloalkyl group, and A represents a nitrogen atom or

wherein $R^3$ represents chlorine atom or cyano group, or a salt thereof.

10. A process for producing a compound represented by formula [$IV_b$]:

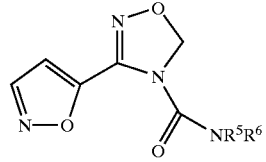

[IVb]

wherein $R^5$ and $R^6$ each represent a $C_{1-6}$ alkyl group, or $R^5$ and $R^6$, together with their adjacent nitrogen atom, represent a cyclic amino group, or a salt thereof, which comprises reacting a compound represented by formula [$IV_a$]:

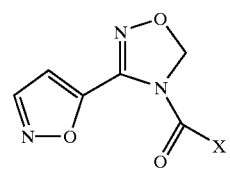

[IVa]

wherein X represents chlorine atom, 1-chloroethoxy group, chloromethoxy group or phenoxy group, or a salt thereof with an amine represented by formula [X]:

[X]

wherein the symbols are as defined above, or a salt thereof.

11. A process for producing a compound represented by formula [$V_a$]:

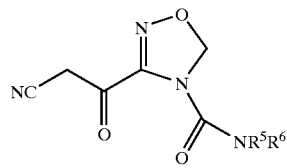

[Va]

wherein $R^5$ and $R^6$ are as defined in claim 10, or a salt thereof, which comprises subjecting a compound represented by formula [$IV_b$]:

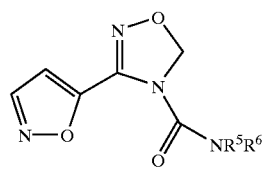

[IVb]

wherein $R^5$ and $R^6$ are as defined in claim 10, or a salt thereof to the ring-opening reaction of the isoxazole ring.

12. A process for producing a compound represented by formula [VII$_a$]:

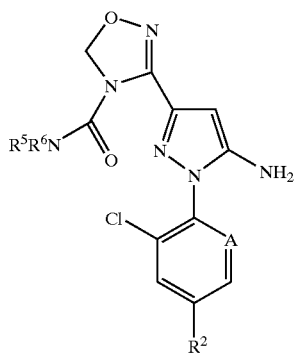

wherein $R^2$ represents (1) halogen, (2) $C_{1-6}$ haloalkyl group, (3) $C_{1-6}$ haloalkoxy group or (4) phenyl group optionally substituted with $C_{1-6}$ haloalkyl group, A represents a nitrogen atom or

wherein $R^3$ represents chlorine atom or cyano group, and $R^5$ and $R^6$ are as defined in claim 10, or a salt thereof, which comprises reacting compound represented by formula [V$_a$]:

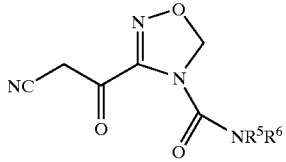

wherein $R^5$ and $R^6$ are as defined in claim 10, or a salt thereof with a compound represented by formula [VI]:

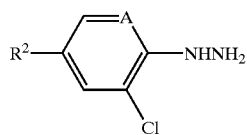

wherein $R^2$ and A are as defined above, or a salt thereof.

13. A process for producing a compound represented by formula [IX$_a$]:

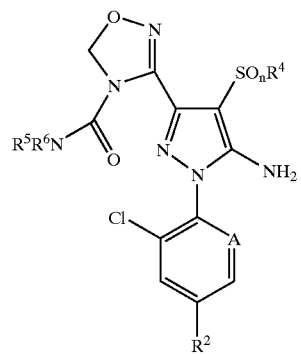

wherein $R^2$ represents (1) halogen, (2) $C_{1-6}$ haloalkyl group, (3) $C_{1-6}$ haloalkoxy group or (4) phenyl group optionally substituted with $C_{1-6}$ haloalkyl group, A represents a nitrogen atom or

wherein $R^3$ represents chlorine atom or cyano group, n is 0, 1 or 2, $R^4$ represents a $C_{1-6}$ alkyl group or a $C_{1-6}$ haloalkyl group, and $R^5$ and $R^6$ are as defined in claim 10, or a salt thereof, which comprises reacting a compound represented by formula [VII$_a$]:

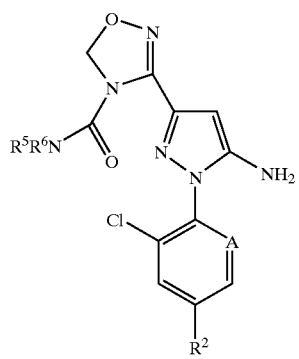

wherein $R^2$ and A are as defined above, and $R^5$ and $R^6$ are as defined in claim 10, or a salt thereof with a compound represented by formula [VIII]:

wherein $R^4$ and n are as defined above, and $X^2$ represents a halogen atom.

14. A compound represented by formula [IV$_a$]:

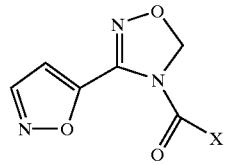

wherein X is as defined in claim 10, or a salt thereof.

15. A compound represented by formula [IV$_b$]:

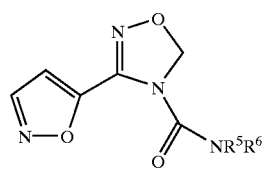

wherein $R^5$ and $R^6$ are as defined in claim 10, or a salt thereof.

16. A compound represented by formula [V$_a$]:

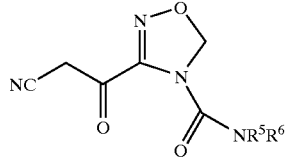
[V$_a$]

wherein R$^5$ and R$^6$ are as defined in claim 10, or a salt thereof.

17. A compound represented by formula [VII$_a$]:

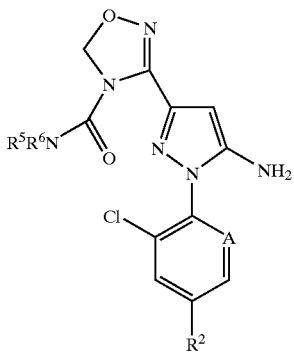
[VII$_a$]

wherein R$^2$ represents (1) halogen, (2) C$_{1-6}$ haloalkyl group, (3) C$_{1-6}$ haloalkoxy group or (4) phenyl group optionally substituted with C$_{1-6}$ haloalkyl group, A represents a nitrogen atom or

wherein R$^3$ represents chlorine atom or cyano group, and R$^5$ and R$^6$ are as defined in claim 7, or a salt thereof.

18. 3-(5-Isoxazolyl)-Δ$^2$-1,2,4-oxadiazoline represented by formula [II]:

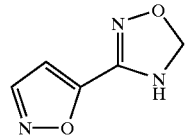
[II]

or a salt thereof.

* * * * *